(12) United States Patent
Schlicker et al.

(10) Patent No.: US 7,049,811 B2
(45) Date of Patent: May 23, 2006

(54) TEST CIRCUIT HAVING PARALLEL DRIVE SEGMENTS AND A PLURALITY OF SENSE ELEMENTS

(75) Inventors: Darrell E. Schlicker, Watertown, MA (US); Neil J. Goldfine, Newtown, MA (US); Andrew P. Washabaugh, Chula Vista, CA (US); Karen E. Walrath, Arlington, MA (US); Ian C. Shay, Cambridge, MA (US); David C. Grundy, Reading, MA (US); Mark Windoloski, Burlington, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 0 days.

(21) Appl. No.: 10/876,002

(22) Filed: Jun. 23, 2004

(65) Prior Publication Data

US 2004/0232911 A1    Nov. 25, 2004

Related U.S. Application Data

(62) Division of application No. 10/102,620, filed on Mar. 19, 2002, now Pat. No. 6,784,662.

(60) Provisional application No. 60/276,997, filed on Mar. 19, 2001.

(51) Int. Cl.
*G01N 27/72* (2006.01)
*G01N 27/82* (2006.01)
*G01R 33/12* (2006.01)

(52) U.S. Cl. .................. 324/242; 324/239; 324/243
(58) Field of Classification Search ........... 324/227, 324/232, 235, 239, 240, 241, 242, 243, 252
See application file for complete search history.

(56) References Cited

U.S. PATENT DOCUMENTS

| | | | |
|---|---|---|---|
| 3,875,502 | A | 4/1975 | Neumaier |
| 5,015,951 | A | 5/1991 | Melcher |
| 5,182,513 | A | 1/1993 | Young et al. |
| 5,262,722 | A | 11/1993 | Hedengren et al. |
| 5,453,689 | A | 9/1995 | Goldfine et al. |
| 5,793,206 | A | 8/1998 | Goldfine et al. |
| 5,966,011 | A | 10/1999 | Goldfine et al. |
| RE36,986 | E | 12/2000 | Melcher |
| 6,188,218 | B1 | 2/2001 | Goldfine et al. |
| 6,657,429 | B1 | 12/2003 | Goldfine et al. |
| 6,727,691 | B1 | 4/2004 | Goldfine et al. |

(Continued)

OTHER PUBLICATIONS

Arbegast, W.J., and Hartley, P.J. (1998), "Friction Stir Weld Technology Development at Lockheed Martin Michoud Space, Systems—An Overview", 5th International EWI Conference on Trends in Welding Research, Jun. 1-5, 1998, Pine Mountain, GA.

(Continued)

*Primary Examiner*—Jay Patidar
(74) *Attorney, Agent, or Firm*—Hamilton, Brook, Smith & Reynolds, P.C.

(57) ABSTRACT

A test circuit having a drive winding with parallel conducting segments and a plurality of sense elements used for the nondestructive measurement of materials. The drive winding segments have extended portions and are driven by a time varying electric current to impose a magnetic field in the test material. Sense elements are distributed in a direction parallel to the extended portions of these drive segments, with separate connections provided to each sense element. A second plurality of sense elements may also be distributed parallel to the extended portions of the drive windings, being either aligned or offset from a first plurality of sense elements.

28 Claims, 35 Drawing Sheets

U.S. PATENT DOCUMENTS

| | | |
|---|---|---|
| 6,798,198 B1 | 9/2004 | Tsukernik et al. |
| 2002/0158626 A1 | 10/2002 | Shay et al. |
| 2002/0163333 A1 | 11/2002 | Schlicker et al. |
| 2004/0124834 A1 | 7/2004 | Goldfine et al. |

OTHER PUBLICATIONS

Auld, B.A. and Moulder, J.C. (1999), "Review of Advances in Quantitative Eddy-Current Nondestructive Evaluation," Journal of Nondestructive Evaluation, vol. 18, No. 1.

Navy Phase I Proposal, titled "Wireless Communications with Electromagnetic Sensor Networks for Nondestructive Evaluation", Topic #N01-174, dated Aug. 13, 2001.

Air Force Phase I Proposal, titled "Three-Dimensional Magnetic Imaging of Damage in Multiple Layer Aircraft Structures", Topic #AF02-281, dated Jan. 14, 2002.

Final Report submitted to FAA, titled "Crack Detection Capability Comparison of JENTEK MWM-Array and GE Eddy Current Sensors on Titanium ENSIP Plates", dated Sep. 28, 2001, Contract #DTFA03-00-C-00026, option 2 CLIN006 and 006a.

Technical Paper titled "Surface Mounted and Scanning Periodic Field Eddy-Current Sensors for Structural Health Monitoring", presented at the IEEE Aerospace Conference, Mar. 2002.

Technical Paper titled "Corrosion Detection and Prioritization Using Scanning and Permanently Mounted MWM Eddy-Current Arrays", presented at the Tri-Service Corrosion Conference, Jan. 2002.

Technical Paper titled "Shaped-Field Eddy Current Sensors and Arrays", presented at the SPIE Conference, Mar. 2002.

Technical paper titled "Residual and Applied Stress Estimation from Directional Magnetic Permeability Measurements with MWM Sensors," submitted to ASME Journal Pressure Vessels and Piping.

Technical paper titled "MWM-Array Characterization and Imaging of Combustion Turbine Components," EPRI International Conference on Advances in Life Assessment and Optimization of Fossil Power Plants, Orlando, FL; Mar. 2002.

Technical presentation slides titled "Scanning and Permanently Mounted Fatigue Test Monitoring and On-Aircraft Monitoring Using Permanently Mounted Eddy-Current Sensor Arrays," USAF ASIP Conference, Williamsburg, VA, Dec. 2001.

Technical presentation slides "Condition Assessment of Engine Component Materials Using MWM-Eddy Current Sensors," ASNT Fall Conference, Columbus, OH; Oct. 2001.

Technical presentation slides "High-Resolution Eddy Current Sensor Arrays with Inductive and Magnetoresistive Sensing Elements," ASNT Fall Conference, Columbus, OH; Oct. 2001.

Techical presentation slides "Surface Mounted MWM-Eddy Current Sensors for Structural Health Monitoring," ASNT Fall Conference, Columbus, OH; Oct. 2001.

Technical paper and presentation slides titled "High Throughput, Conformable Eddy-Current Sensor Arrays for Engine Disk Inspection including Detection of Cracks at Edges and in Regions with Fretting Damage," NASA/FAA/DoD Conference on Aging Aircraft, Kissimmee, Florida; Sep. 2001.

Technical paper and presentation slides titled "High-Resolution Eddy Current Sensor Arrays for Detection of Hidden Damage including Corrosion and Fatigue Cracks," NASA/FAA/DoD Conference on Aging Aircraft, Kissimmee, Florida; Sep. 2001.

Technical paper titled "Flexible Eddy Current Sensors and Scanning Arrays for Inspection of Steel and Alloy Components," 7th EPRI Steam Turbine/Generator Workshop and Vendor Exposition, Baltimore, MD; Aug. 2001.

Technical paper titled "Conformable Eddy-Current Sensors and Arrays for Fleet-wide Gas Turbine Component Quality Assessment," ASME Turbo Expo Land, Sea & Air, New Orleans, Louisiana; Jun. 2001.

Technical presentation slides titled "Friction Stir Weld LOP Defect Detection Using New High-Resolution MWM-Arrays and MWM Eddy-Current Sensors," Aeromat 2001 Conference; Jun. 2001.

Technical paper titled "Applications for Conformable Eddy Current Sensors including High Resolution and Deep Penetration Sensor Arrays in Manufacturing and Power Generation," ASME 7th NDE Topical Conference, San Antonio, Texas; 2001.

Technical paper titled "Surface Mounted Periodic Field Eddy Current Sensors for Structural Health Monitoring," SPIE Conference: Smart Structures and Materials NDE for Health Monitoring and Diagnostics, Newport Beach, California; Mar. 2001.

Technical paper and presentation "Scanning and Permanently Mounted Conformable MWM Eddy Current Arrays for Fatigue/Corrosion Imaging and Fatigue Monitoring," USAF ASIP Conference, San Antonio, TX, Dec. 2000.

Technical presentation slides "Inspection of Gas Turbine Components Using Conformable MWM Eddy-Current Sensors," ASNT Fall Conference, Indianapolis, Indiana; Nov. 2000.

Technical paper titled "Anisotropic Conductivity Measurements for Quality Control of C-130/p-3 Propeller Blades Using MWM Sensors with Grid Methods," Fourth DoD/FAA/NASA Conference on Aging Aircraft, St. Louis, MO; May 2000.

Technical paper titled "Surface-Mounted Eddy-Current Sensors for On-Line Monitoring of Fatigue tests and for Aircraft Health Monitoring," Second DoD/FAA/NASA Conference on Aging Aircraft, Aug. 1998.

Technical paper titled "Early Stage Fatigue Detection with Application to Widespread Fatigue Damage Assessment in Military and Commerical Aircraft," First DoD/FAA/NASA Conference on Aging Aircraft, Ogden, UT, Jun. 1997.

Technical paper "Combustion Turbine Blade Coating Characterization Using a Meandering Winding Magnetometer," ASNT Fall Conference, 1994.

TEST CIRCUIT HAVING PARALLEL DRIVE SEGMENTS AND A PLURALITY OF SENSE ELEMENTS

RELATED APPLICATION

This application is a divisional of U.S. application Ser. No. 10/102,620 filed Mar. 19, 2002, now U.S. Pat. No. 6,784,662 which claims the benefit of U.S. Provisional Application No. 60/276,997 filed Mar. 19, 2001, the entire teachings of which are incorporated herein by reference.

BACKGROUND

The technical field of this invention is that of nondestructive materials characterization, particularly quantitative, model-based characterization of surface, near-surface, and bulk material condition for flat and curved parts or components using eddy-current sensors. Characterization of bulk material condition includes (1) measurement of changes in material state caused by fatigue damage, creep damage, thermal exposure, or plastic deformation; (2) assessment of residual stresses and applied loads; and (3) assessment of processing-related conditions, for example from shot peening, roll burnishing, thermal-spray coating, or heat treatment. It also includes measurements characterizing material, such as alloy type, and material states, such as porosity and temperature. Characterization of surface and near-surface conditions includes measurements of surface roughness, displacement or changes in relative position, coating thickness, temperature and coating condition. Each of these also includes detection of electromagnetic property changes associated with single or multiple cracks. Spatially periodic field eddy-current sensors have been used to measure foil thickness, characterize coatings, and measure porosity, as well as to measure property profiles as a function of depth into a part, as disclosed in U.S. Pat. Nos. 5,015,951 and 5,453,689.

Conventional eddy-current sensing involves the excitation of a conducting winding, the primary, with an electric current source of prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

In many inspection applications, large surface areas of a material need to be tested. This inspection can be accomplished with a single sensor and a two-dimensional scanner over the material surface. However, use of a single sensor has disadvantages in that the scanning can take an excessively long time and care must be taken when registering the measured values together to form a map or image of the properties. These shortcomings can be overcome by using an array of sensors or an array of elements within a single sensor, as described for example in U.S. Pat. No. 5,793,206, since the material can be scanned in a shorter period of time and the measured responses from each array element are spatially correlated. However, the use of arrays complicates the instrumentation used to determine the response of each array element. For example, in one conventional method, as described for example in U.S. Pat. No. 5,182,513, the response from each element of an array is processed sequentially by using a multiplexer for each element of the array. While this is generally faster than scanning a single sensor element, there is still a significant time delay as the electrical signal settles for each element and there is the potential for signal contamination from previously measured channels.

For nondestructive testing of conducting and/or magnetic materials over wide areas, eddy current sensor arrays may be used. These eddy current sensors excite a conducting winding, the primary, with an electrical current source of a prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks. When scanning over wide areas, these arrays may include several individual sensors, but each sensor must be driven sequentially in order to prevent cross-talk or cross-contamination between the sensing elements.

Eddy current arrays have also been disclosed in U.S. Pat. No. 5,262,722, however the implemented versions of these arrays use differential sensing elements. The use of differential sensing element, that essentially compare the response of two neighboring sensing regions, limits the capability to determine absolute properties of interest. These sensor arrays and conventional eddy current sensors are also highly sensitive to sensor position, requiring expensive automated scanners to build images of material properties for complex surface inspections. Differential sensors may also produce false indications on relatively rough surfaces, such as surfaces with fretting damage.

SUMMARY

Aspects of the inventions described herein involve novel sensors for the measurement of the near surface properties of conducting and/or magnetic materials. These sensors use novel geometries for the primary winding and sensing elements that promote accurate modeling of the response and provide enhanced capabilities for the creation of images of the properties of a test material.

In one embodiment, sensor array designs are disclosed that permit the creation of property images when scanned over a material surface. In one embodiment, the drive winding includes at least one central conducting segment and parallel return segments located on either side to impose a periodic magnetic field of at least two spatial wavelengths in a test material, a linear array of sensing elements to sense the response to the test material properties, and at least one sensing element uses a magnetoresistive (MR) or giant magnetoresistive (GMR) sensor. Secondary coils can also be placed around one or more of the MR or GMR sense elements, in one embodiment. In another, these coils are connected in a feedback configuration, and, in one embodiment, act to maintain the magnetic field at the MR or GMR sensor at a prescribed level.

In another embodiment of a sensor array design, the drive winding includes at least one central conducting segment and at least one parallel return segment on either side, a linear array of sensing elements between the central segments and a return segment, and separate connections to each sensing element. The distance between the central segments and the return segments can be selected to align with features of interest in a test material, such as bolt holes. One embodiment includes two central conductors and a return path for each conductor, with equal distances between the central conductors and each return path. In another embodiment, a second linear array of sensing elements is placed between another pair of linear drive winding segments, parallel to the first linear array. In one form, each element in the first array is aligned with an element in the second array. In another form, elements in the first array are offset from the elements in the second array in a direction parallel to the linear drive winding segments. Preferably, this offset distance is one-half of the length of a sense element, which ensures complete coverage of the element in a direction perpendicular to the drive winding segments. In an embodiment, the linear arrays are equally distant from the central conductors. Differential measurements may also be taken in the response between elements in the first array and elements in the second array. The central conductors can be placed in the same plane as the sensing elements to improve the coupling with the sense elements.

In an embodiment, the conductivity and proximity of the sensing elements to the surface are measured to detect cracks. In another, the proximity of each sensing element to the test material surface is used to determine surface roughness. In another embodiment, the sensing element response is used for health monitoring or condition assessment of a component. An embodiment also includes the use of a characteristic sensor response for a flaw and using that characteristic response to construct a filter. This filter can be applied to a response image to emphasize indications that are likely to be associated with flaws and suppresses indications unlikely to be associated with flaws.

In one embodiment, a single encoder determines the position of the array while scanning. In another embodiment, an automated scanner is used to move the array over a test material. In another embodiment, using modular fixtures with position encoders facilitates manual scanning of complex parts. In an embodiment, a template is used to align incremental scans over a test material so that images of the material properties over areas wider than the array width can be generated.

To facilitate the scanning of a sensor array over a material test surface, another embodiment includes the use of a fluid filled balloon. In an embodiment, this balloon is attached to a shuttle and the shuttle is shaped to approximately match the shape of the test material. In another embodiment, the sensor and balloon components are modularized and can be replaced rapidly. In one embodiment, the inspection is performed on the surface of a bolt hole. In another, the inspection is performed on the inside of an engine disk slot.

In another embodiment of a sensor array design, the drive winding includes at least one pair of parallel conducting segments to impose a magnetic field in the test material, a linear array of sensing elements, and separate connections to each sensing element. The distance between the parallel segments can be selected to align with features of interest in a test material. In one form, the linear array is placed between the parallel segments of the drive. Preferably, in another form, the array is placed outside the loop formed by the parallel segments of the drive. This also permits both the drive segments and the sense elements to be placed in the same plane.

In another embodiment, a second linear array of sensing elements is placed parallel to the first linear array of elements. This second array can be placed between the parallel segments of the drive winding, near a segment of the drive winding common with the first array. In another embodiment, the second array is placed outside the drive winding loop, opposite that of the first array. The distances between the linear arrays and the drive winding segments can be selected to be the same or different. In one embodiment, each element in the first array is aligned with an element in the second array. In another embodiment, elements in the first array are offset from the elements in the second array in a direction parallel to the linear drive winding segments. Preferably, this offset distance is one-half of the length of a sense element.

In an embodiment for the sensor array, the locations of the sensing elements in a direction parallel to the drive segments and the sensing element size can be made non-uniform to provide a higher image resolution over specific material test areas. In another embodiment, the sensor array can be fabricated onto a flexible substrate so that the sensor can conform to the shape of the test material. Alternatively, the sensor array can be fabricated onto a rigid substrate. With either substrate material, measurements of the material properties can be performed in a noncontact fashion. In an embodiment, at least one of the sensing elements includes a MR or GMR sensor. In one form, these sensing elements also include a secondary coil. In another form, the secondary coil is used in a feedback configuration.

In yet another embodiment, a sensor array design comprises two parallel linear rows of sensing elements on opposite sides of a central conductor for detecting cracks on each side of a feature. In one embodiment this feature is a fastener in an aircraft skin. In another embodiment, multiple frequency measurements are used to remove interference cause by the feature itself to isolate and emphasize the response of the crack. An embodiment also includes using the sensor response from a sensing element to create a characteristic response for a flaw and to construct a filter. This filter can be applied to a response image to emphasize indications that are likely to be associated with flaws and suppresses indications unlikely to be associated with flaws. In one form, the flaw is a crack. In another, the flaw is a buried inclusion.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows. The design and use of high resolution conformable eddy current sensor arrays is described for the nondestructive characterization of materials. These sensor arrays are well suited to inspections over wide areas as a single scan of the sensor array allows the material properties to be determined over a relatively wide distance. Also, sequential scans can be concatenated, with or without overlap, to create images over wide areas. Furthermore, simple manual scans can be used with only a roller encoder to record position, still producing two-dimensional images of the quality previously achieved with high cost automated scanners. Measurements of the responses from each element in a linear array of sensing elements, oriented perpendicular to the scan direction, also facilitates the creation of material property images so that the presence of property variations or defects are readily apparent.

Figure 1:
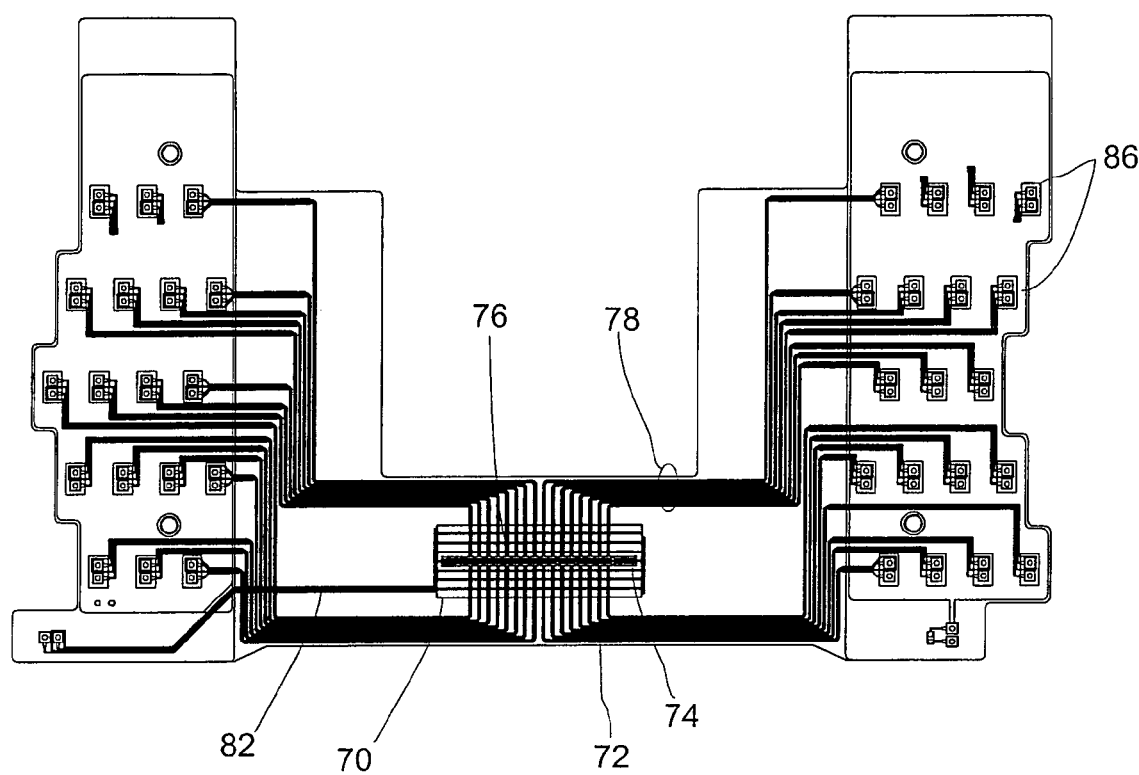
FIG. 1 is a drawing of a spatially periodic eddy current sensor array.
Figure 2:
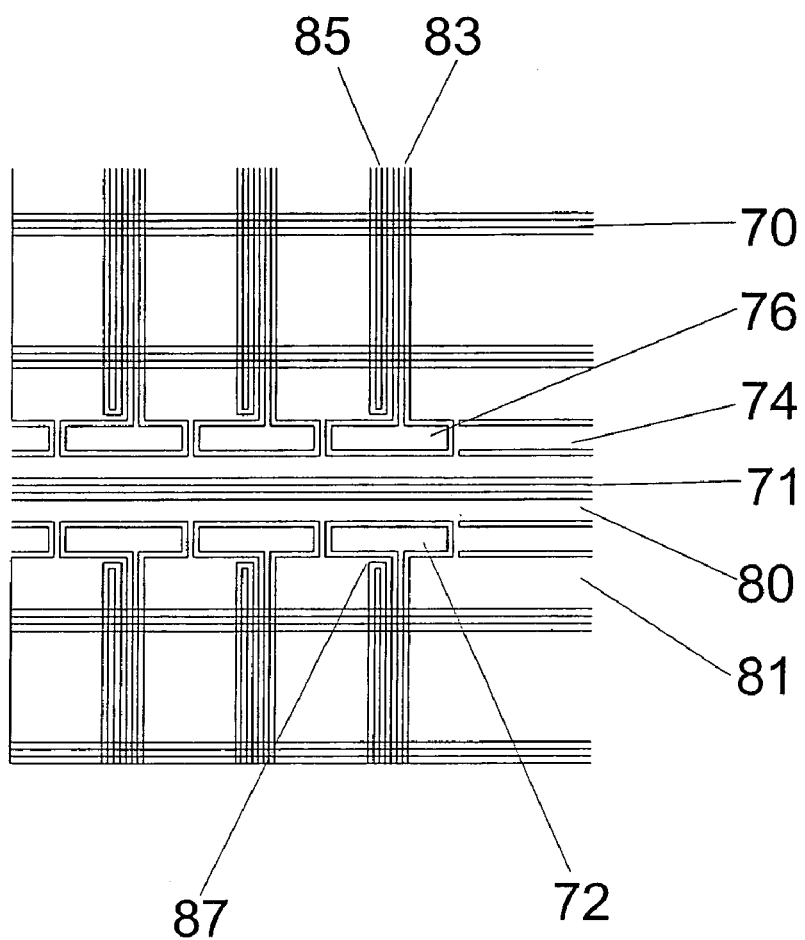
FIG. 2 is an expanded view of the drive and sense elements for the spatially periodic eddy current sensor array shown in FIG. 1.
Figure 3:
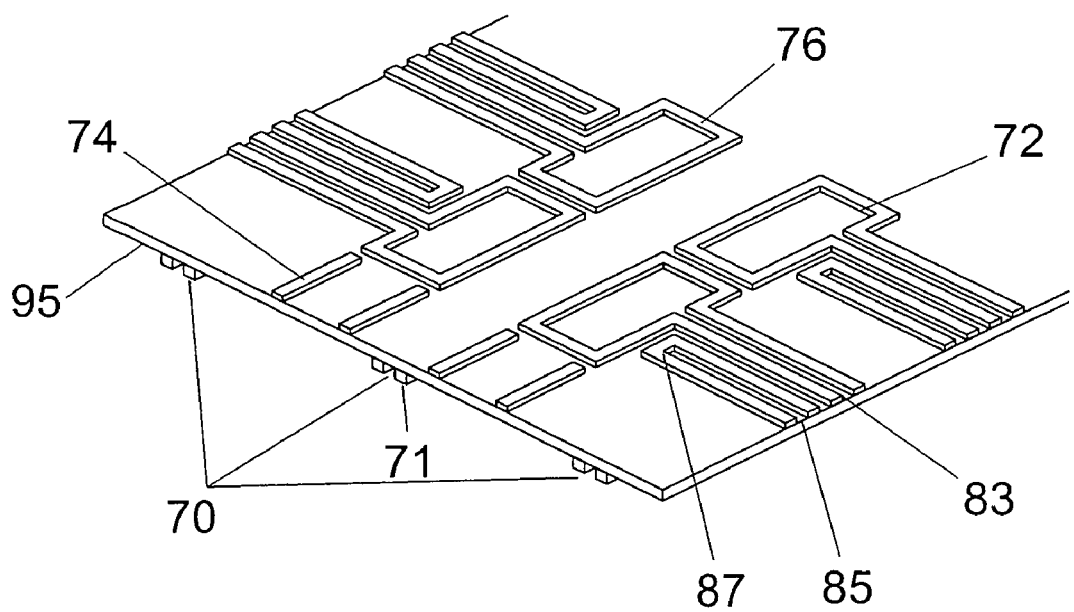
FIG. 3 is a pictorial cross-sectional view of some of the drive and sense elements for the sensor of FIG. 1.

In one embodiment, eddy current sensor arrays with at least one meandering drive winding and multiple sensing elements are used to inspect the test material. An example sensor array is shown in FIG. 1. Expanded views of the region near the sensing elements are shown in FIG. 2 and FIG. 3. This array includes a spatially periodic primary winding 70 having extended portions for creating the magnetic field and a plurality of secondary elements 72 within the primary winding for sensing the response to the material under test (MUT). The primary winding is fabricated in a periodic pattern with the dimension of the spatial periodicity termed the spatial wavelength $\lambda$. This geometry can be described as a meandering winding so that a single element sensor, where all of the sensing elements are connected together, can be called a Meandering Winding Magnetometer (MWM®) and a sensor array having a similar primary winding an MWM-Array, as described in U.S. patent application Ser. No. 10/010,062, filed Nov. 13, 2001, the entire teachings of which are incorporated herein by reference.

Melcher first conceived the use of meandering or rectangular drives with multiple sensing regions and drive wires connected in series to cover a significant area, as described in U.S. Pat. No. 5,015,951. Detailed descriptions of this geometry for an eddy current sensor are given in U.S. Pat. Nos. 5,453,689, 5,793,206, and 6,188,218. In U.S. Pat. No. 5,262,722, a similar approach to Melcher's is used to link series connected drive regions to excite differential sensing elements. In the MWM sensors, a time-varying current is applied to the primary winding, which creates a magnetic field that penetrates into the MUT and induces a voltage at the terminals of the secondary elements. This terminal voltage reflects the properties of the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218. The magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. Nos. 5,793,206 and Re. 36,986 and also U.S. application Ser. No. 09/666,879, filed Sep. 20, 2000, now U.S. Pat. No. 6,657,429, the entire teachings of which are incorporated herein by reference, and U.S. application Ser. No. 09/666,524, filed Sep. 20, 2000, the entire teachings of which are incorporated herein by reference.

The MWM structure can be produced using micro-fabrication techniques typically employed in integrated circuit and flexible circuit manufacture. This results in highly reliable and highly repeatable (i.e., essentially identical) sensors, which has inherent advantages over the coils used in conventional eddy-current sensors which exhibit significant sensor-to-sensor variability even for nominally identical sensors. As indicated by Auld and Moulder, for conventional eddy-current sensors "nominally identical probes have been found to give signals that differ by as much as 35%, even though the probe inductances were identical to better than 2%" (Auld, 1999). The lack of reproducibility with conventional coils introduces severe requirements for calibration of the sensors (e.g., matched sensor/calibration block sets). In contrast, duplicate MWM sensor tips have nearly identical magnetic field distributions around the windings as standard micro-fabrication (etching) techniques have both high spatial reproducibility and resolution. As the sensor was also designed to produce a spatially periodic magnetic field in the MUT, the sensor response can be accurately modeled which dramatically reduces calibration requirements. For example, in some situations an "air calibration" can be used to measure an absolute electrical conductivity without calibration standards, which makes the MWM sensor geometry well-suited to surface mounted or embedded applications where calibration requirements will be necessarily relaxed.

An efficient method for converting the response of the MWM sensor into material or geometric properties is to use grid measurement methods. These methods map the magnitude and phase of the sensor impedance into the properties to be determined and provide for a real-time measurement capability. The measurement grids are two-dimensional databases that can be visualized as "grids" that relate two measured parameters to two unknowns, such as the conductivity and lift-off (where lift-off is defined as the proximity of the MUT to the plane of the MWM windings). For the characterization of coatings or surface layer properties, three-dimensional versions of the measurement grids can be used. Alternatively, the surface layer parameters can be determined from numerical algorithms that minimize the least-squares error between the measurements and the predicted responses from the sensor.

An advantage of the measurement grid method is that it allows for real-time measurements of the absolute electrical properties of the material. The database of the sensor responses can be generated prior to the data acquisition on the part itself, so that only table lookup operation, which is relatively fast, needs to be performed. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations and instrument preparation.

While a single meandering conductor can be used for the primary winding, this leads to the formation of a large inductive loop that can influence the eddy current sensor response. Splitting the primary winding so that the return leads to each component of the drive winding are in close proximity to one another can substantially reduce the effects of this extraneous inductive loop. In FIG. 1, FIG. 2 and FIG. 3, the primary winding 70 is split into two parts so that each extended portion of a primary winding meander, except for the endmost, includes two conducting elements. Each loop of the primary winding is connected together in series and the primary windings are wound so that the current through adjacent conductors is in the same direction. The current through these two conducting loops imposes a spatially periodic magnetic field. This winding configuration minimizes the effects of stray magnetic fields from the lead connections to the primary winding, which can create an extraneous large inductive loop that influences the measurements, maintains the meandering winding pattern for the primary, and effectively doubles the current through the extended portions of the meanders. This method for reducing the effects of the extraneous loop is described more completely in U.S. application Ser. No. 09/666,879, now U.S. Pat. No. 6,657,429, and Ser. No. 09/666,524.

Figure 20:
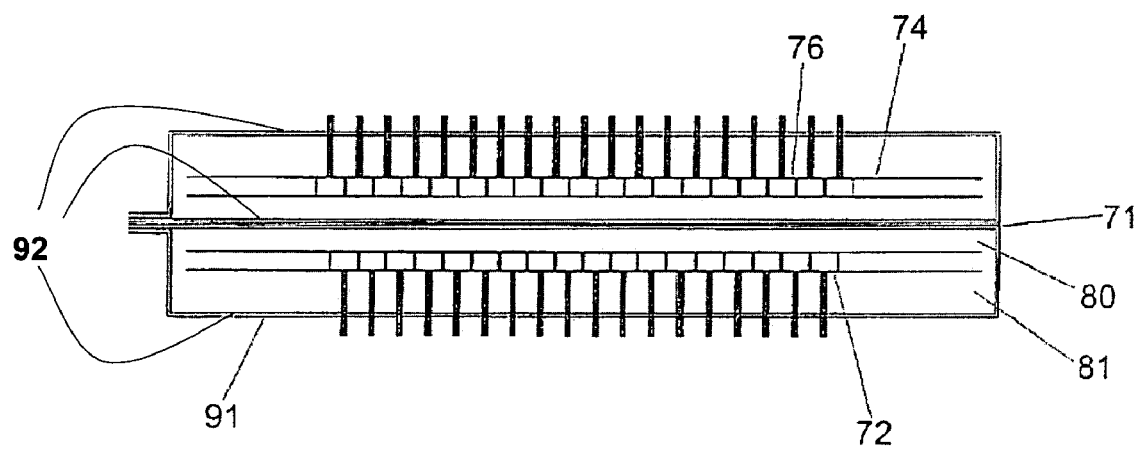
FIG. 20 is an expanded view of the drive and sense elements for an eddy current array having offset rows of sensing elements.

When the sensor is scanned across a part or when a crack propagates across the sensor, perpendicular to the extended portions of the primary winding, secondary elements 76 in a primary winding loop adjacent to the first array of sense elements 72 provide a complementary measurement of the part properties. These arrays of secondary elements 76 are aligned with the first array of elements 72 so that images of the material properties will be duplicated by the second array. Alternatively, to provide complete coverage when the sensor is scanned across a part the sensing elements 76 can be offset along the length of the primary loop or when a crack propagates across the sensor, perpendicular to the extended portions of the primary winding, secondary elements 76 in a primary winding loop adjacent to the first array of sense elements 72 can be offset along the length of the primary loop, as illustrated in FIG. 20. Additional primary winding meander loops, which only contain dummy elements, are placed at the edges of the sensor to help maintain the periodicity of the magnetic field. The connection leads 78 to the secondary elements are perpendicular to the extended portions of the primary winding, which necessitates the use of a multi-layer structure in fabricating the sensor. The layers that contain the primary and secondary winding conductors are separated by a layer of insulation. Layers of insulation are generally also applied to the top and bottom surfaces of the sensor to electrically insulate the primary and secondary windings from the MUT. A protective layer is also sometimes used, e.g. Kapton™ or Teflon™ with or without a removable adhesive. This layer becomes sacrificial, protecting the sensor and being periodically removed and replaced with age.

The leads to the primary and secondary elements are kept close together to minimize fringing field coupling. The leads 82 for the primary winding are kept close together to minimize the creation of fringing fields. The leads 78 for the secondary elements are kept close together to minimize the linkage of stray magnetic flux. The bond pads 86 provide the capability for connecting the sensor to a mounting fixture. The bond pads 86 are spread out for easier design, contact, and assembly of the connectors to the bond pads. The trace widths for the primary winding can also be increased to minimize ohmic heating, particularly for large penetration depths that require low frequency and high current amplitude excitations. Also, the conducting primary thickness and width may be increased to minimize ohmic heating.

Figure 4:
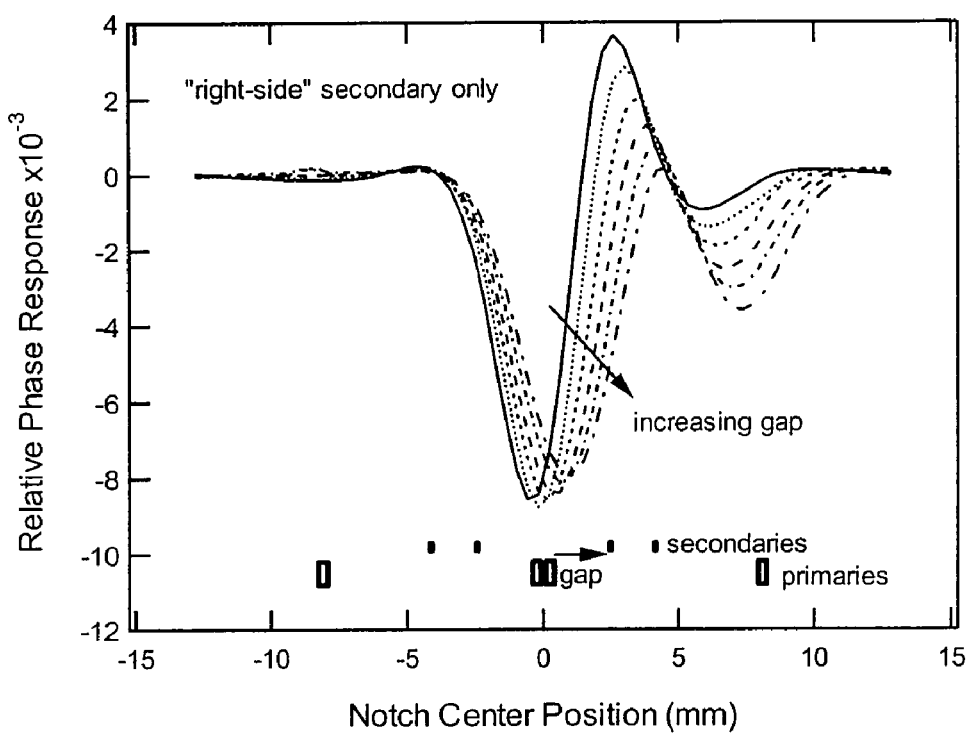
FIG. 4 is a plot of the calculated sensor response to a notch as the gap between the sensing elements and the central primary conductors is varied.
Figure 21:
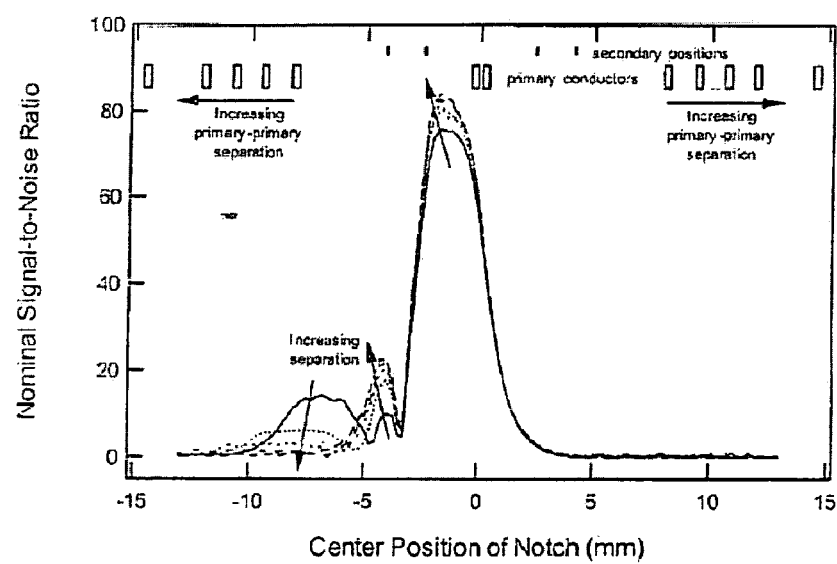
FIG. 21 is a plot of the calculated response to a surface breaking notch using a model, indicating the response to the secondary element on the left side of the central conductor.

The placement of the sensing elements near the primary windings can also be adjusted to enhance sensitivity to specific types of flaws or defects. FIG. 2 shows an expanded view around the sensing elements for the sensing array of FIG. 1. The arrays of sensing elements 72 and 76 are located relatively close to the common portions of the primary winding 70 so that the distance 80 is smaller than the distance 81. Past MWM designs emphasized placing the sensing elements at the center of the gap between the primary winding legs, so that the distances 80 and 81 were equal, to minimize coupling of short spatial wavelength magnetic field modes. With the previous design, scanning the sensor array over a small (compared to a half-wavelength) surface breaking or near-surface defect leads to a double-humped response from the sensing element, with each hump occurring when the drive windings nearest to the sensing elements are predominantly over the defect. Physically, for a conducting MUT, the time varying magnetic field induces eddy currents in the MUT that mirror the conductor pattern of the primary winding and these induced eddy currents are largest beneath the primary windings. The presence of a defect interrupts this current flow and the perturbations in the magnetic field are detected with the sensing elements. With the new offset secondary design (distances 80 and 81 unequal), the response to the defect will be asymmetric with an enhanced response when the defect is beneath the common or central primary winding 70 and a reduced response when the defect is beneath the further or return primary windings. FIG. 4 illustrates this effect. Modeling was performed to calculate the response in the relative phase change as a flaw, in this case a rectangular notch, passes beneath a single element of an array. Increasing the gap between the central conductor and the return winding causes a decrease in the response peaks for flaw locations beneath the central primary conductor and the secondaries but an increase in the response peak for flaw locations beneath the return winding. The response when the defect is beneath the return portion of the primary winding can be reduced by moving the return winding further away from the sensing elements, as shown in FIG. 21. Reducing the response from the return is an advantage when trying to build images and improve reliability.

The arrays of sensing elements 72 and 76 are offset the same distance 80 from the common primary winding 71 to maintain the capability for obtaining the same measurement from a given defect. Material property variations and orientation of non-spherical defects can affect the responses of the sensing elements in each array differently, which provides the potential to separate defect features and defect signals from background property variations. A simple filter would be to sum the responses of spatially correlated sensing elements (when the scanning direction is perpendicular to the extended portions of the primary winding), which would highlight the presence of defects when underneath the common drive winding 71. Furthermore, filters can compare the sensing element responses to ensure that the spatially correlated sensing elements are responding to the same feature. In addition, the responses of neighboring sensing elements can be used to normalize the response, eliminating background variations of the material properties. Multiple frequency measurements can also be used to enhance the results.

Figure 5:
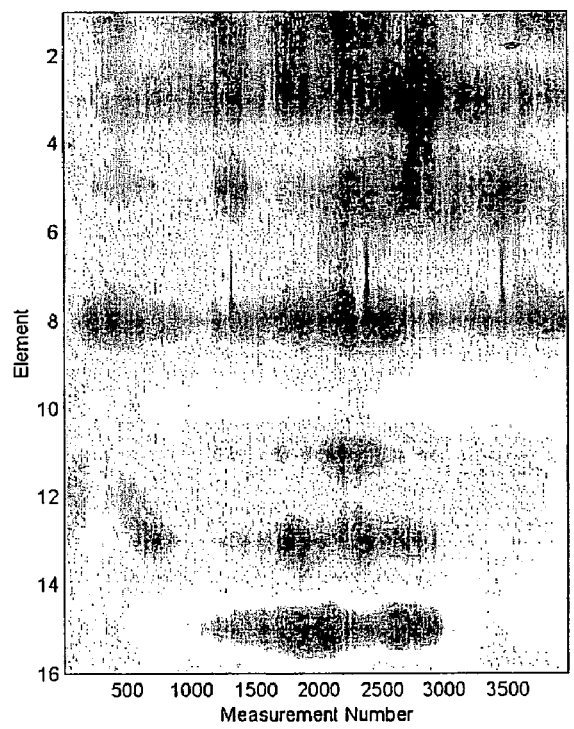
FIG. 5 is an unfiltered measurement image taken with an eddy current sensing array over a Titanium alloy plate containing cracks at a frequency of 8 MHz.
Figure 6:
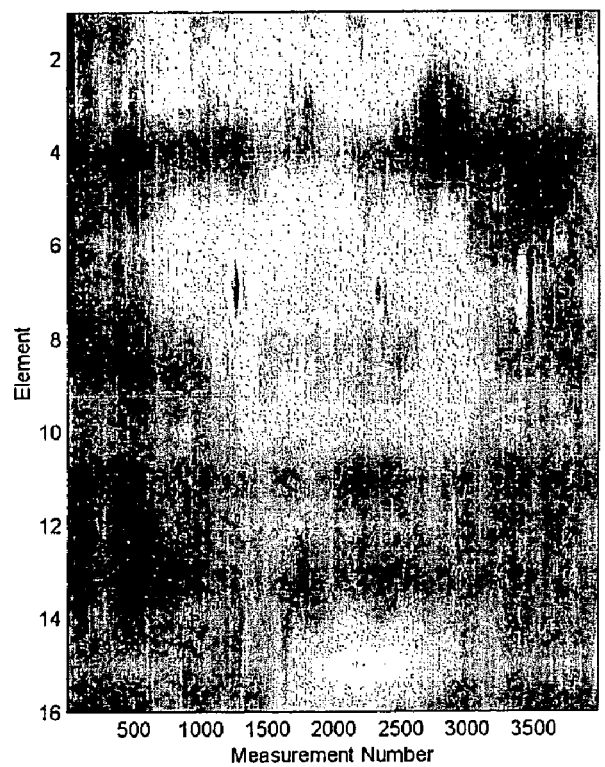
FIG. 6 is an unfiltered measurement image taken with an eddy current sensing array over a Titanium alloy plate containing cracks at a frequency of 12 MHz.

The distinct shapes of the sensor response when passing over a flaw can be isolated using "matched filters" as described in application Ser. No. 10/010,062, now abandoned. Then, by searching an image for this distinctive shape the response to a local defect can be enhanced. As an example, this process is illustrated in FIG. 5 through FIG. 10 for cracks in a Titanium alloy flat crack standard. Unfiltered images of the effective conductivity images from a scan over the standard are shown in FIG. 5 for an 8 MHz excitation and in FIG. 6 for a 12 MHz excitation. On this particular standard, there are three cracks of lengths 0.711, 0.635, and 0.686 mm (0.028, 0.025, and 0.027-inches, respectively) along the path of element 7. A filtered image, shown in FIG. 7, has highlighted cracks and suppressed background noise variations.

Figure 8:
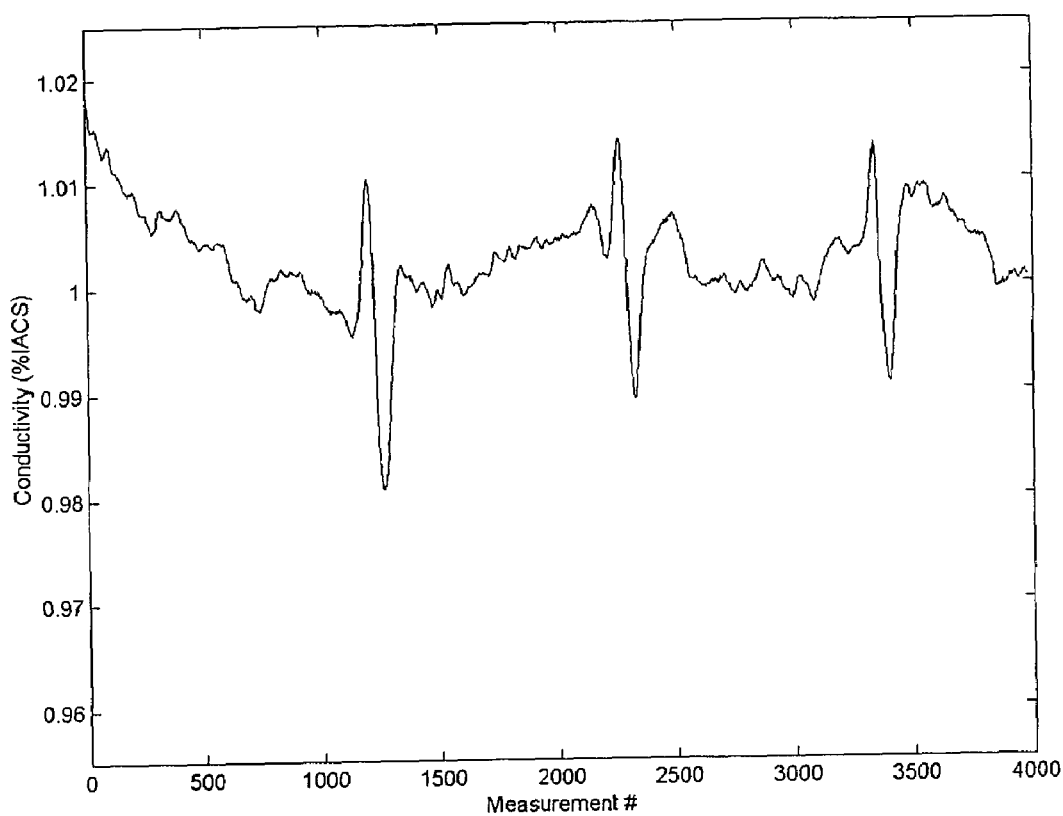
FIG. 8 is a plot of the unfiltered 8 MHz sensor response from element 7 in the trailing row of elements in the array used to scan over a Titanium alloy plate containing cracks.
Figure 9:
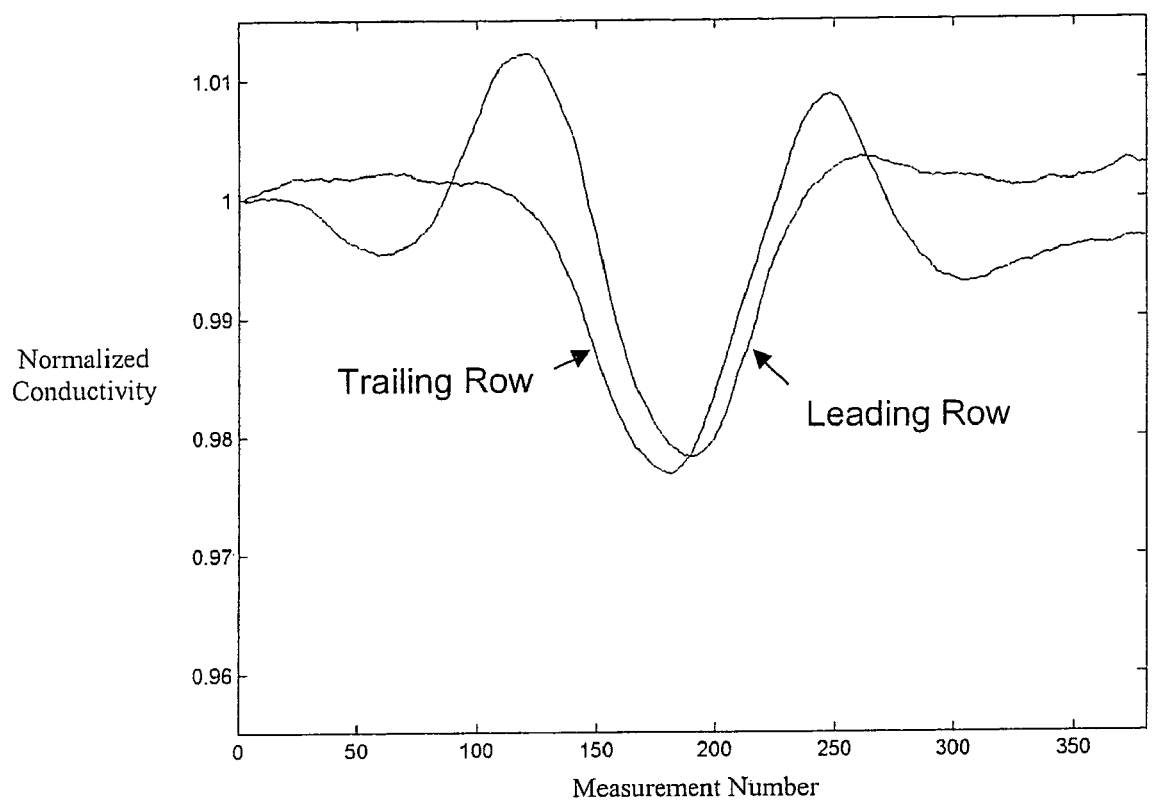
FIG. 9 is a plot of the 8 MHz sensor response to a single crack in a Titanium plate.

In this case the filtered image combines the response from both the trailing and leading rows of sensing elements at both measurement frequencies into a single response. This is accomplished for each row (trailing and leading) and measurement frequency (8 MHz and 12 MHz) by first calculating, element-by-element, the correlator of a moving window of data with a shape filter. For example FIG. 8 shows the unfiltered 8 MHz data from element 7 in the trailing row and FIG. 9 shows the trailing row shape response. Similar responses are used for the leading row data and the 12 MHz data. The resulting signal can be denoted $x_1(i,j)$ where the index i denotes element number and j denotes the measurement number. Repeating this process yields $x_2(i,j)$ for the 8 MHz leading row data, $y_1(i,j)$ for the 12 MHz trailing row data, and $y_2(i,j)$ for the 12 MHz leading row data. The results from each row of the 8 MHz data are then combined as $$x(i, j) = \frac{(x_1(i, j) + x_2(i, j))}{2 * 2^{(x_1(i,j) - x_2(i,j))}}$$

and the results from each row of the 12 MHz data are then combined as $$y(i, j) = \frac{(y_1(i, j) + y_2(i, j))}{2 * 2^{(y_1(i,j) - y_2(i,j))}}$$

Then, the results from each frequency are combined as $$z(i, j) = \frac{(x(i, j) + y(i, j))}{2 * 2^{(x(i,j) - y(i,j))}}$$

Figure 7:
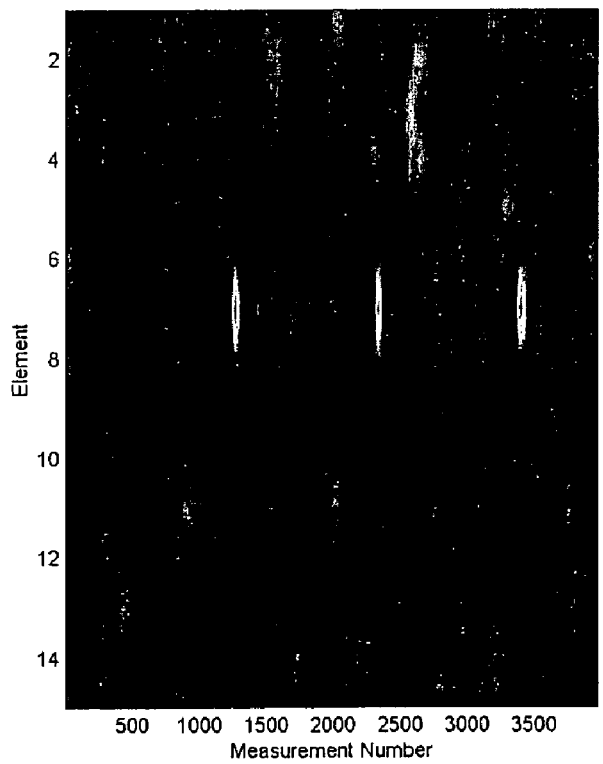
FIG. 7 is a filtered measurement image that combines the data of FIG. 5 and FIG. 6 to highlight the cracks.
Figure 10:
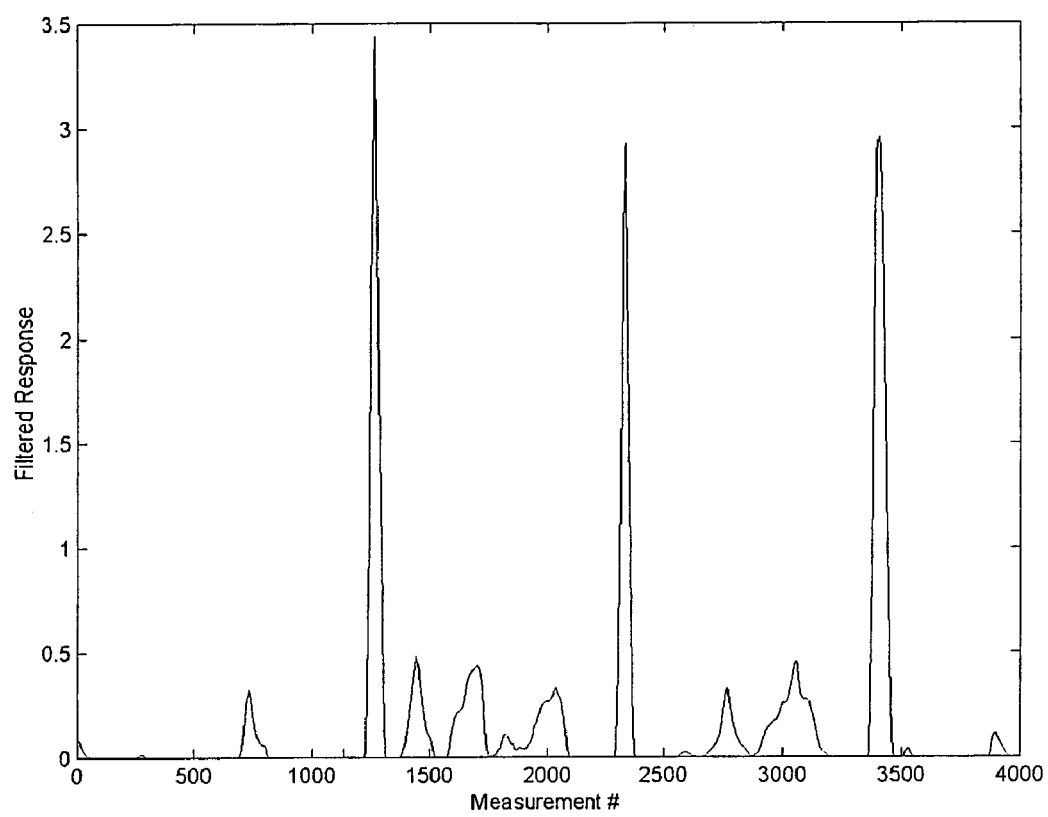
FIG. 10 is a plot of the filtered sensor response from element 7 using the shape responses like those of FIG. 9 and both measurement frequencies.

This result is shown in FIG. 10 for element 7 alone and in FIG. 7 for all of the elements. Note that this particular procedure suppresses signals on one row of elements but not the other row, at a given frequency. It also suppresses signals that appear on only one frequency but not the other. This improves clutter suppression to limit false alarms.

FIG. 2 and FIG. 3 also show that the connection leads 83 to each sensing element are closely paralleled by another set of leads 85 ending in a closed loop 87. As described in U.S. application Ser. No. 09/666,879, now U.S. Pat. No. 6,657,429, and Ser. No. 09/666,524, the differential response between the actual sensing element and the parallel leads 85 is measured. This "flux cancellation" configuration provides a measure of the absolute signal in the vicinity of the sensing element and helps to minimize the effects of stray inductive and capacitive coupling to the sensing element leads. The use of flux cancellation allows longer lead lines to be used, permits the spreading out of connection leads 83 so that standard pins can be used for the connections and eliminates cross-talk problems encountered in closely packed connection schemes, and also allows the sensor part of the probe to incorporate a connection board. The elimination of tightly packed connectors is a significant cost and durability advantage. Furthermore, this use of a differential measurement to obtain absolute signal responses from the sensing elements permits calibration in air, where calibration coefficients are obtained from comparisons of the sensor signal in air to the predicted response for the sensor based on a model for the sensor geometry. This then permits an absolute measurement of the electromagnetic and geometric properties of the MUT, such as electrical conductivity, magnetic permeability and layer thickness) without the use of calibration standards. Of course, the sensor or sensor arrays can also be calibrated on reference standard having known properties. In contrast, the use of conventional differential and absolute eddy current sensors requires performing calibration measurements on reference standards to set the gain levels for this instrumentation before quantitative MUT property information can be obtained. In this design the primary windings 70 are separated from the secondary element arrays 72 and 76 by a layer of insulation 95. This layer of insulation is typically 0.5 to 1 mil (12.7 to 25.4 micrometers) thick Kapton™.

Figure 11:
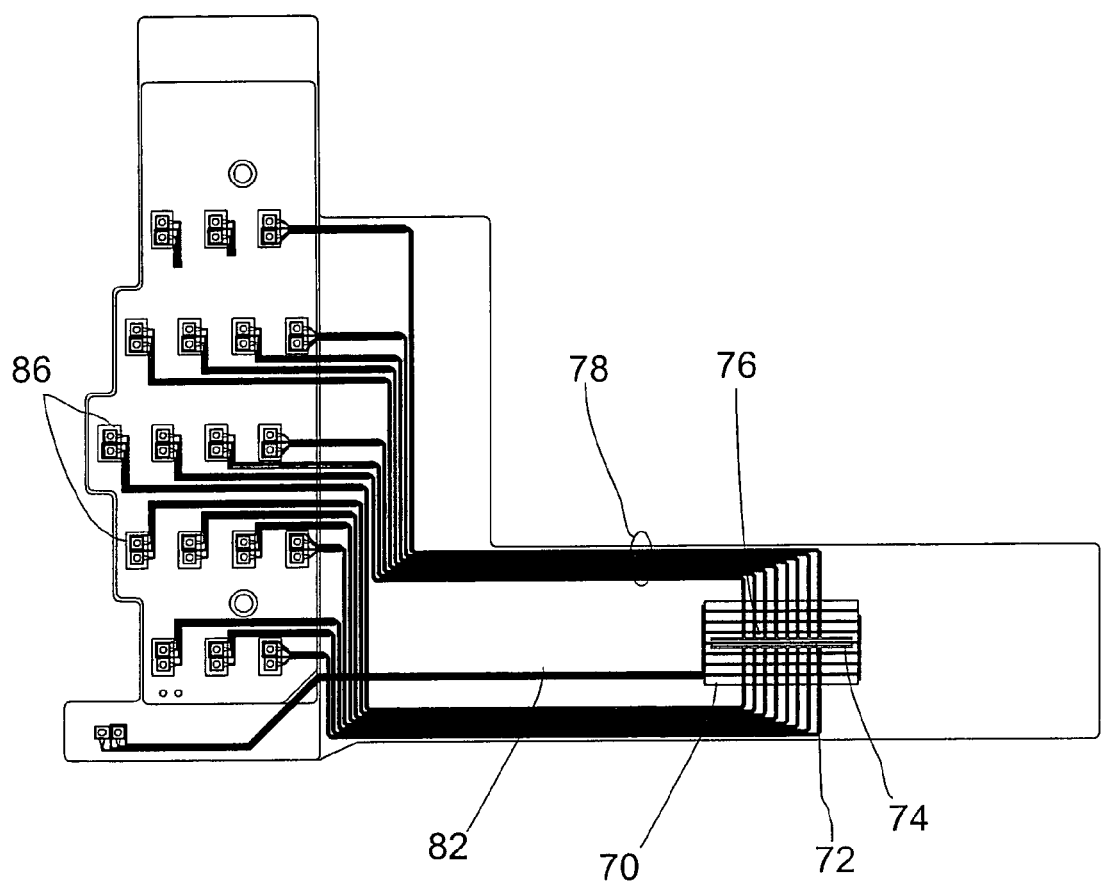
FIG. 11 is a drawing of a spatially periodic field eddy current sensor array having all connection leads on one side of the array.
Figure 14:
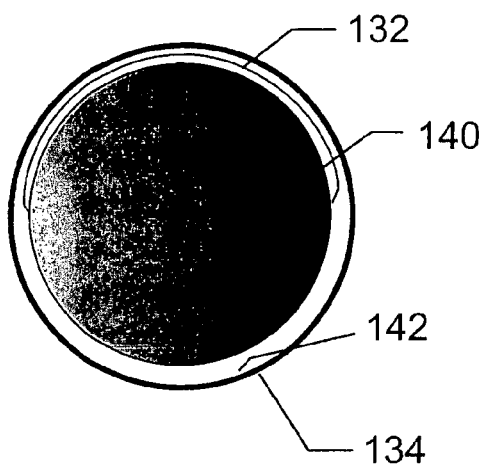
FIG. 14 is a cross-sectional view of an eddy current sensing array inside a pipe.

FIG. 11 shows another configuration for an MWM-Array. In this case all of the leads 78 to the sensing element arrays and the leads 82 to the primary winding are on one side of the sensor. This allows the active area of the sensor, defined by the area covered by the primary windings 70 to be inserted into confined areas such as bolt holes or disk slots. Scanning of the array in a direction perpendicular to the extended portions of the primary winding, which could require rotating the sensor in a bolt hole, allows complete coverage of the inspection area. The sensor might also be oriented with the extended portions of the primary windings at a right angle to that shown or as shown with the sensing region offset relative to the connector to permit insertion into geometric features such as the inside surface of pipes, bolt holes, and gun barrels, which is illustrated in FIG. 12 and FIG. 14.

Figure 12:
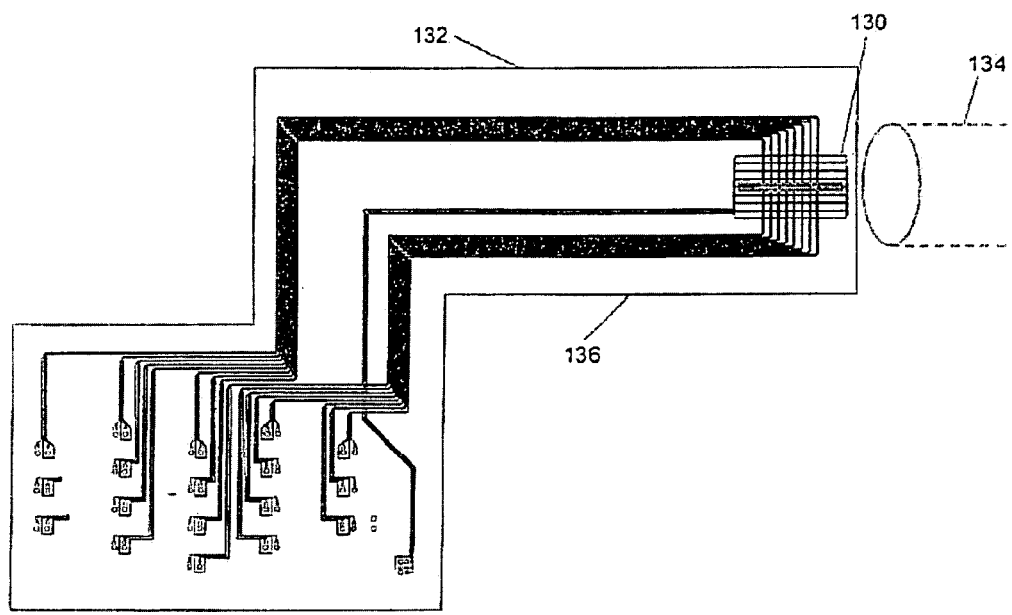
FIG. 12 is a drawing of an eddy current sensing array being near an opening in a test material.
Figure 13:
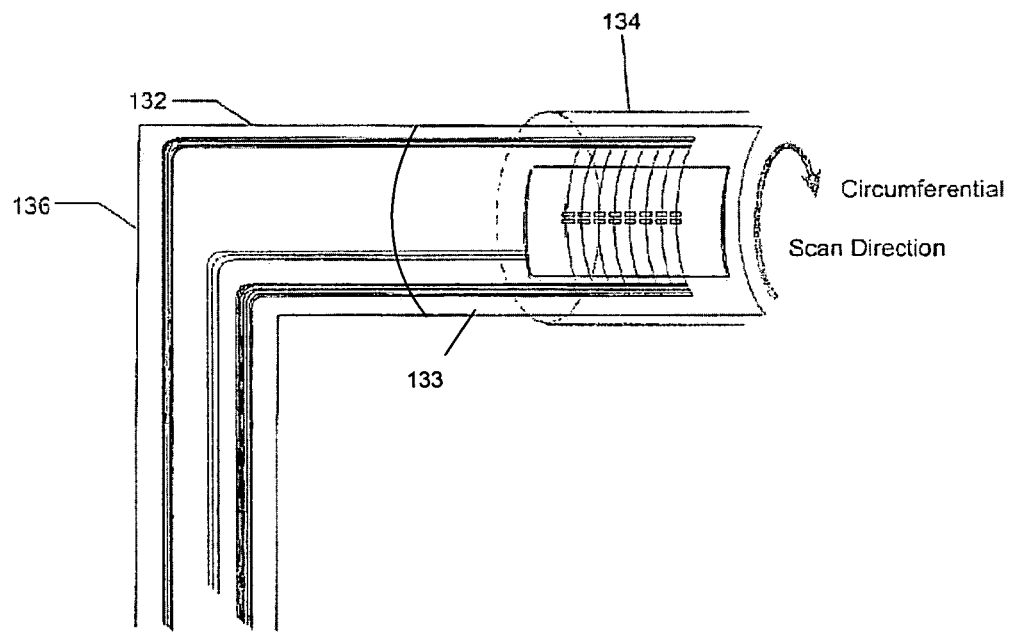
FIG. 13 is a drawing of an eddy current sensing array being inserted into a pipe.

In FIG. 12, the array 132 has a sensing array 130 offset from the connector (with numerous bond pads) parallel to the direction of the longest dimension of the connector. The extended portions of the primary winding for creating the magnetic field are parallel to the offset direction of the array. Two arrays of sensing elements are placed at the center of and run parallel to the extended portions of the primary winding. The sensing array is fabricated onto a flexible Kapton™ lining or substrate 136, which permits the shape of the sensing structure to be deformed for insertion of the eddy current sensing array into confined areas 134 such as pipes and bolt holes to inspect for defects and damage. The conformability of the sensing array inside the confined space is illustrated in FIG. 13. FIG. 14 shows a cross-sectional view of the sensor inside this space. The sensor 132 can be held against the inside surface 142 of the test material 134 with a foam or balloon support 140. This support provides both a reasonably rigid framework for holding the sensing structure in-place when inserted into the hole and also a compliant backing for maintaining intimate contact between the sensing structure and the inside surface of the test material. The sensor array 130, and ballon support 140 may be rapidly replaced with a removable cartidge 133. Rotating the sensing structure in a circumferential direction, perpendicular to the extended portions of the primary winding, then permits complete coverage of the surface of the test material during the inspection. The inspection can also be performed with the sensing structure placed at different distances into the pipe so that pipe lengths greater than the length spanned by the sensing element arrays can be inspected. This also allows multiple measurements of a given area to be performed. The distance into the pipe can be monitored with a position encoder or controlled with a robotic arm to permit accurate measurements of the insertion distance into the pipe.

Figure 15:
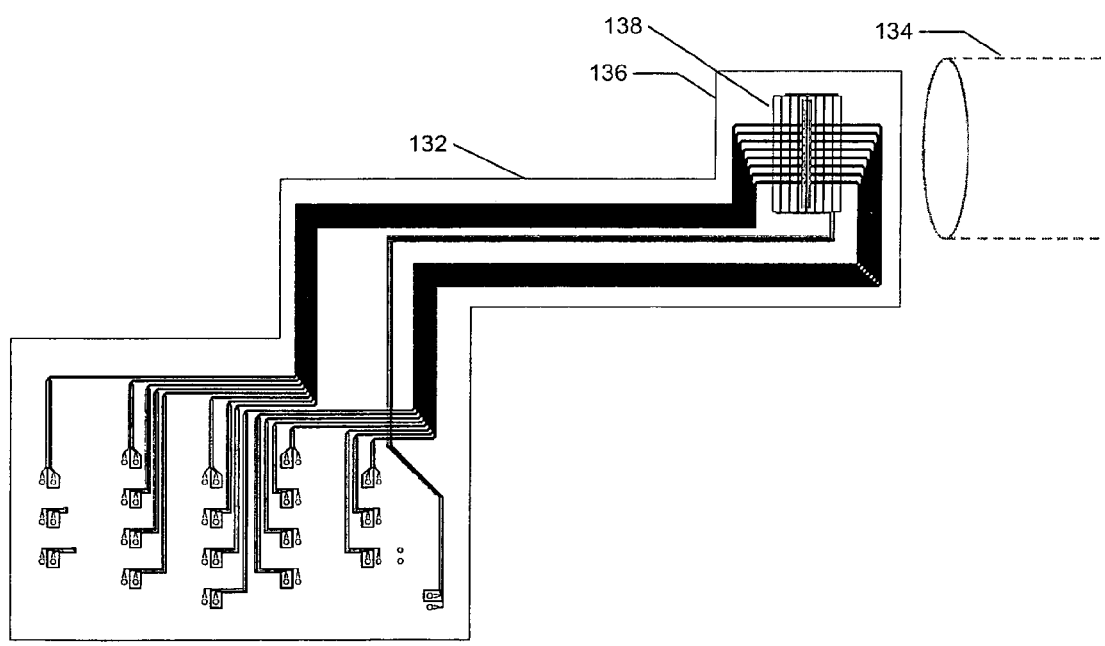
FIG. 15 is another drawing of an eddy current sensing array being near an opening in a test material.
Figure 16:
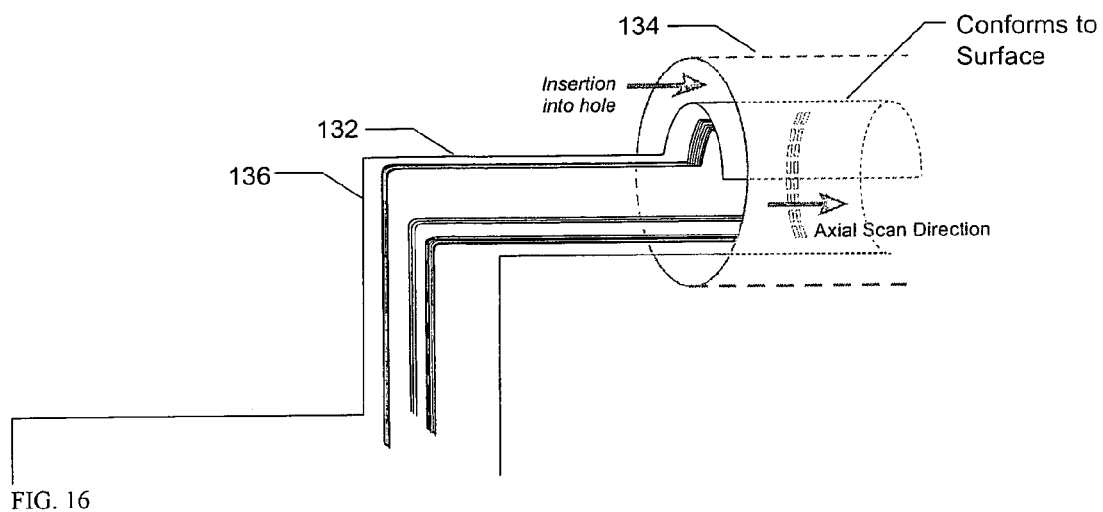
FIG. 16 is another drawing of an eddy current sensing array being inserted into a pipe.

FIG. 15 shows another embodiment for the inspection of confined areas such as a pipe. In this case the extended portions of the primary winding, and the arrays of sensing elements 138, are oriented perpendicular to the offset direction of the sensing structure from the connector. Again, the sensing structure is mounted onto a foam or balloon substrate which allows the sensing structure to conform to the surface of the test material when inserted into a pipe or other confined space, as illustrated in FIG. 16. Here, moving the sensing structure in an axial direction, perpendicular to the extended portions of the primary winding, then permits complete coverage of the surface of the test material under the sensing elements during the inspection. Measurement scans at different angular positions along the circumference of the hole can then provide a complete inspection of the entire hole surface.

Figure 17:
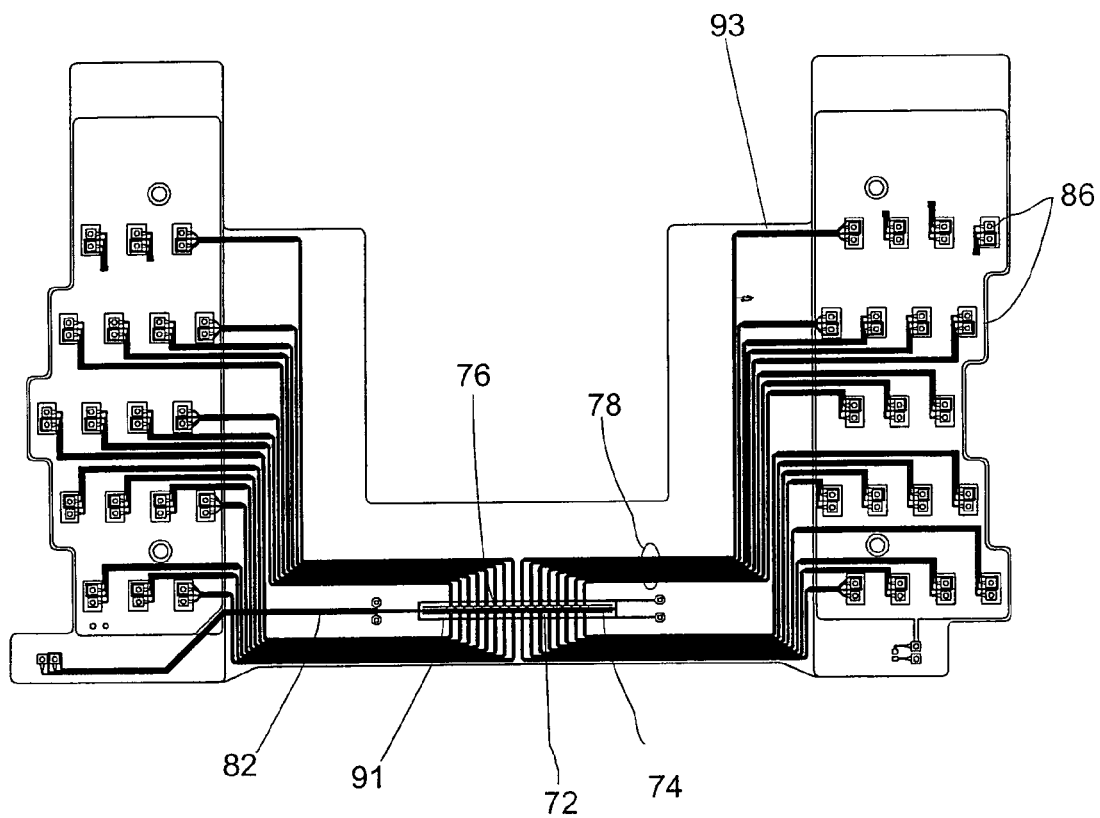
FIG. 17 is a drawing of a single wavelength eddy current sensor array.
Figure 18:
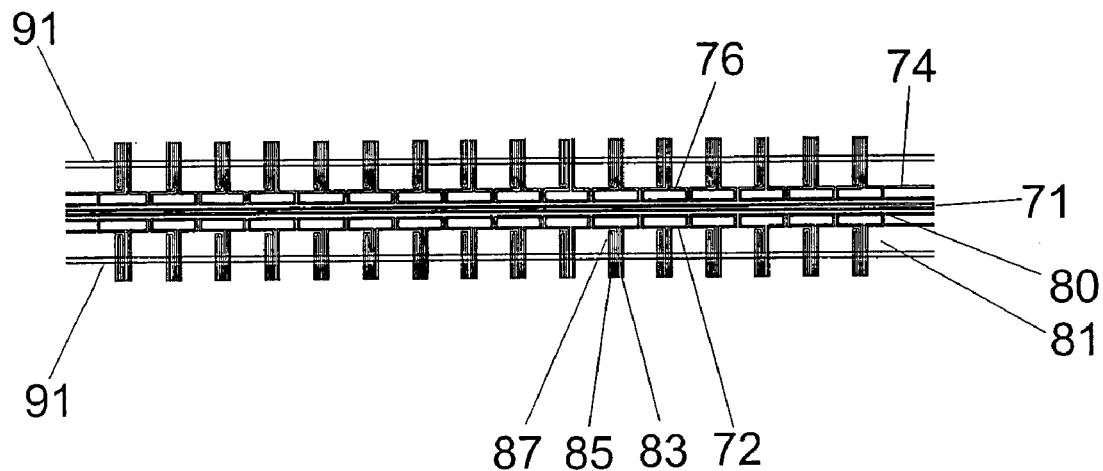
FIG. 18 is an expanded view of the drive and sense elements for the eddy current array shown in FIG. 17.
Figure 19:
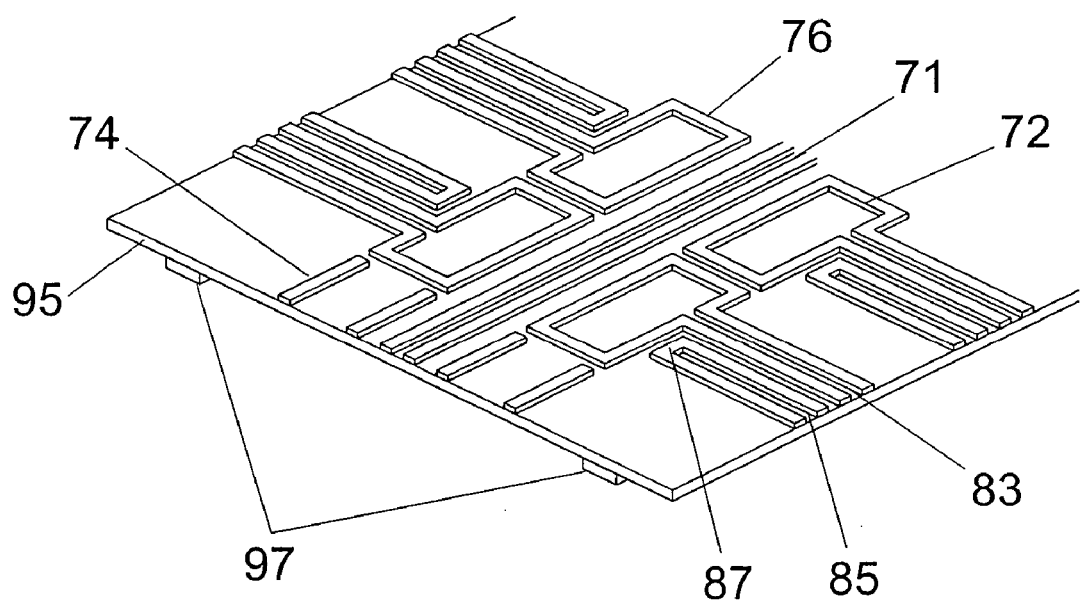
FIG. 19 is a pictorial cross-sectional view of the drive and some of the sense elements for the eddy current array shown in FIG. 17.

FIG. 17 shows another embodiment for an MWM-Array, with an expanded view of the primary meanders and the sensing elements in FIG. 18 and FIG. 19. In this case, the number of primary winding meanders 91 is reduced so that measurements can be performed closer to material edges without affecting the sensor response. The primary conductors 91 of FIG. 17 and FIG. 18 show a single wavelength for a primary winding meander. The secondary element arrays 72 and 76 are brought close to the central conductors of the primary 71, so that the gap 80 between the extended portions of the primary and secondary windings is smaller than the gap 81. In this region, the magnetic field distribution is similar to the spatially periodic magnetic field distribution of a primary winding having more than one meander. As described in U.S. application Ser. No. 09/666,879, now U.S. Pat. No. 6,657,429, and Ser. No. 09/666,524, as well as U.S. application Ser. No. 09/891,091, filed Jun. 25, 2001, now abandoned, the entire teachings of which are incorporated herein by reference, this structure still has the leads for the primary and the secondary close to one another and the split primary winding design has two conductors in the central region 71 which also eliminates the presence of large, extraneous external loops for linking magnetic flux.

To help reduce the series resistance for the connection leads 78 and 82 the conductors are made wider in regions 93 far from the sensing region determined by the extended portions of the primary winding 91. This reduction in series resistance reduces the ohmic heating of the primary winding when driven by the alternating current.

Reducing the number of extended portions of the primary winding meanders has several advantages. First, since sensing elements are closer to the endmost primary winding conductors, measurements can be performed closer to the edge of a material before extended portions of the primary winding go off the material edge and affect the measured signal. Second, the inductance of the primary winding circuit or the drive impedance also decreases so that it is easier to drive current through the primary, at a given voltage, at high frequencies such as 10 to 30 MHz. Third, the sensing element leads 83 cross-over a smaller number of primary winding conductors, which, in addition to the use of the parallel conducting loops 85, reduces the susceptibility to electrical noise and undesired, stray magnetic flux distant from the sensing element. The capability to measure at higher frequencies combined with the flux cancellation lead design (83, 85, 87) permit use of smaller sensing elements with low noise instrumentation, as described in U.S. application Ser. No. 10/010,062. These smaller elements (1) improve sensitivity to small defects, (2) increase the resolution for imaging internal geometric features, such as cooling holes, corrosion or pitting, (3) reduce edge effects, (4) improve surface topology mapping capabilities, and (5) improve coverage and quality in imaging the quality of processes such as shot peening, coating thickness and porosity, case hardening, and grinding.

Another feature illustrated in FIG. 19 is that the central portion of the primary winding 71 and the arrays of sensing elements 72 and 76 lie in the same plane. The return legs for the primary winding 97 are on a different plane and connected to the central portion conductors 71 with vias at the ends of the primary winding half-meanders. This allows for direct connections to the sensing elements with a minimum number of vias, which improves both reliability and manufacturability at a reasonable cost. Placing the critical portions of the sensor, the central portion of the primary winding and the secondary elements, on the same plane also allows higher precision fabrication processes to be used. For example, standard fabrication techniques have placement tolerances between copper paths on the same layer of 3 mils (75 micrometers). In contrast, the layer to layer alignment tolerance for copper paths is normally up to 5 mils (125 micrometers). This improves the manufacturing reproducibility of the sensor array. Placing the central portion of the primary windings and the secondary elements on the same plane also provides enhanced sensitivity to cracks and defects. One reason is that the distance between the primary and the secondary elements is smaller than when the primary windings are in the back plane, which increases the inductive coupling between the primary and the secondary. Another reason is that the eddy currents induced by the applied field are larger when the primary is closer to the MUT.

In a similar fashion, the central portion of the primary winding could also be placed in the same plane as the secondary elements for the arrays having more than one meandering, as in FIG. 1 and FIG. 11. This would provide the benefit of increased sensitivity to defects and only require via connections at the ends of the central primary windings. The remaining extended portions of the primary windings can not be in the plane of the secondary elements because they would interfere with the layout or pathways for the connection leads to the sensing elements.

In another embodiment, the linear rows of sensing elements can be offset from one another, as shown in FIG. 20, so that scanning of the array in a direction perpendicular to the sensing elements ensures complete coverage of the MUT and no defects are missed in the gaps between sensing elements. The drive on this array comprises two loops having extended portions 92 and connected in series so that thecurrent in each of the conductors 71 in the center of the drive is in the same direction.

The effective spatial wavelength or the distance between the central conductors 71 and the current return conductor 91 can be altered to adjust the sensitivity of a measurement for a particular inspection. For example, a sensor array such as FIG. 20 can be scanned over the surface of an MUT to inspect for surface breaking flaws or flaws hidden beneath material layers. For the sensor array of FIG. 20, the distance 80 between the secondary elements 72 and the central conductors 71 is smaller than the distance 81 between the sensing elements 72 and the return conductor 91. Modeling can be performed to calculate the response of the flaw as it passes beneath a single element of the array, as shown in FIG. 21. This two-dimensional analysis assumed a given plate thickness, a conductivity 17.4 MS/m, a lift-off of 0.15 mm, and a rectangular surface breaking notch. The position of the return conductor was also set in the model. The transimpedance between the secondary on one side of the central conductor and the drive current was calculated for various positions beneath the sensor array and used to determine a signal-to-noise-ratio using the formula $$SNR = \sqrt{\left(\frac{m-m_o}{n_m}\right)^2 + \left(\frac{p-p_o}{n_p}\right)^2}$$

where m denotes the transimpedance magnitude, p denotes the transimpedance phase, the subscript o denotes response from the original unflawed material distant from the flaw, and n denotes the noise in the instrument response. This noise is determined empirically for existing sensors and assumed to be constant as the geomtry of the sensor is varied.

Figure 22:
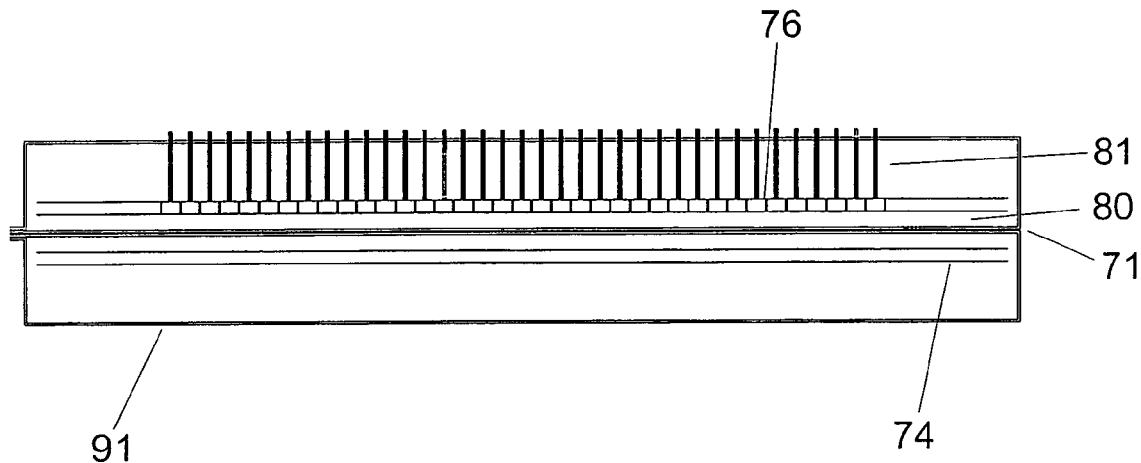
FIG. 22 is an expanded view of the drive and sense elements for an eddy current array having a single row of sensing elements.

The simulation results of FIG. 21 illustrate how the primary-to-primary distance can affect the response of the sensor as it passes over a flaw. With the standard primary-to-primary distance, FIG. 21 shows a large indication when the flaw is between the central drive winding segments and the sensing element. There is also a significant peak in the response when the flaw is nearly beneath the return leg of the primary winding and a minor peak above the outer conductor for the secondary winding. As the primary-to-primary separation distance is increased, the primary peak increases slightly and the peak associated with the return leg of the primary is reduced. This is desirable because a larger signal is obtained from the flaw and the reduction in the distant peak helps to reduce the appearance of "ghost" signals in scan images, where multiple indications are shown for a single flaw. The minor peak above the outer conductor for the secondary winding is also enhanced as the primary-to-primary distance is increased so that more of the signal is concentrated in the vicinity of the sensing secondary element, which again reduces the "ghosting" effect. An example of a modified sensor design is shown FIG. 22. In this sensor array, all of the sensing elements 76 are on one side of the central drive windings 71. The size of the sensing elements and the gap distance 80 to the central drive windings 71 are the same as in the sensor array of FIG. 20. However, the distance 81 to the return of the drive winding has been increased, as has the drive winding width to accommodate the additional elements in the single row of elements.

In some applications, such as aircraft lap joint inspection for cracks or corrosion or weld inspection for stress or defects, it is desirable to map or image the properties of the MUT across the entire region of interest with a single scan pass and for extended distances. Raster scanning a single element sensor across the zone of interest and down the length of the inspection region can provide a high resolution image of the MUT properties both across and along the inspection region, but is very time consuming. In contrast, longitudinal scanning with a linear array of sensing elements, which provides information about the MUT properties in the transverse direction, can be much more efficient. The number, size and location of the sensing elements in the array determine the transverse resolution of the property image created by the array across the inspection region. The scan speed and data acquisition rate determine the resolution in the longitudinal, scan, direction. When there are characteristic features of the MUT properties across the inspection region that indicate the quality of the region, the array of sensing elements can be tailored for that particular type of inspection.

As an example, consider the inspection of a friction stir weld (FSW). The formation of an FSW is characterized by complex metal flow patterns and microstructural changes. Three distinctly different major zones can be typically identified as: (1) a dynamically recrystallized zone (DXZ), or weld nugget, (2) a thermomechanical or heat- and deformation-affected zone (TMZ), adjacent to the weld nugget on both leading and trailing sides of the joint, and (3) a heat-affected zone (HAZ) (Arbegast, 1998; Ditzel, 1997). The two types of defects that have been noted in friction stir welds are: (1) tunnel defects within the nugget and (2) lack of penetration (LOP) (Arbegast, 1998). LOP exists when the DXZ does not reach the backside of the weld due to inadequate penetration of the pin tool. The LOP zone may also contain a well-defined cracklike flaw such as a cold lap, which is formed by distorted but not bonded original faying, i.e., butt, surfaces. This occurs as a result of insufficient heat, pressure and deformation. However, the LOP can be free of well-defined cracklike flaws, yet not be transformed by the dynamic recrystallization mechanism since temperatures and deformation in the LOP may not be high enough. Although it may contain a tight "kissing bond," this second type of LOP defect is the most difficult to detect with alternative methods such as phased-array ultrasonic or liquid penetrant inspection.

Figure 23:
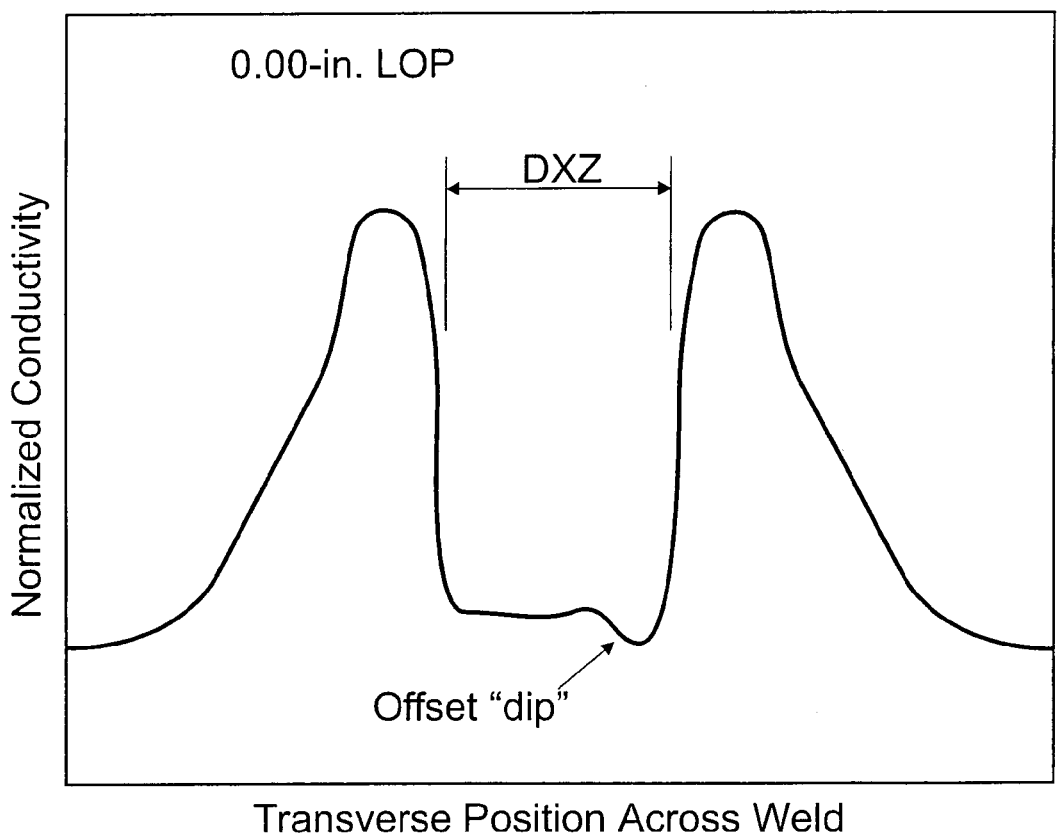
FIG. 23 is a schematic of the normalized conductivity for a measurement channel of a high-resolution MWM-Array with longer segments of the primary winding oriented parallel to the weld axis for a similar metal zero LOP defect specimen.

For an FSW, the quality of the weld or the joint between the base materials can be determined from features in the measurements of the electrical conductivity profile across the joint region, as described in more detail in U.S. application Ser. No. 09/891,091, now abandoned, as well as in U.S. application Ser. No. 10/046,925, filed Jan. 15, 2002, the entire contents of which are incorporated herein by reference. For example, planar flaws can appear as sharp reductions in the electrical conductivity and, for some alloys, the width of the peaks in the electrical conductivity profile can provide a measure of the DXZ width and LOP. Local reductions or dips in the electrical conductivity near the edges of the DXZ, as illustrated in FIG. 23, can also provide information about the quality of the weld. In order to inspect these welds, the sensor array needs to be wide enough to cover the entire weld region. In addition, differences in the base material properties, such as the electrical conductivity, can drastically affect the property profile across the weld, so it is important to have sense elements outside the weld zone.

Figure 24:
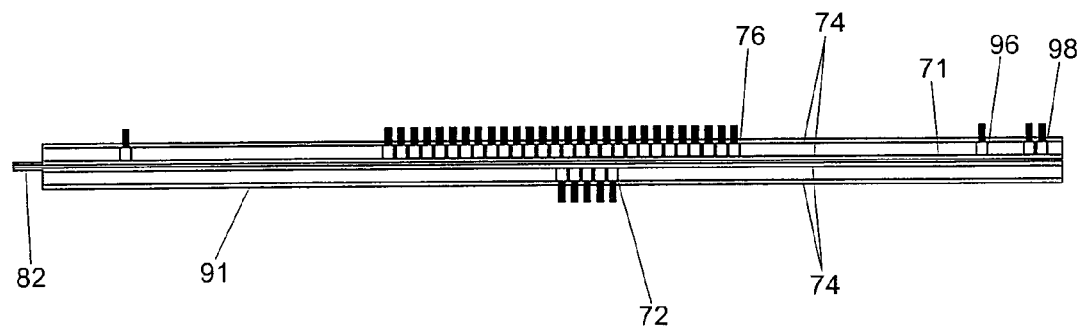
FIG. 24 is an expanded view of an eddy current array where the locations of the sensing elements along the array are staggered.

A sensor array embodiment suitable for FSW inspection is shown in FIG. 24. Here, most of the sensing elements 76 are located in a single row to provide the basic image of the material properties. A small number of sensing elements 72 are offset from this row to create a higher image resolution in this location, which is the location of a "dip" in electrical conductivity near the edge of the DXZ. In addition, several other sensing elements 96 and 98 are located a distance away from the main grouping of sensing elements in order to obtain measurements of the base material properties of the plates being joined. Alternatively, the size of the elements in the different regions could also be varied. Other combinations or groupings of the sensing elements are also within the scope of this description.

Figure 25:
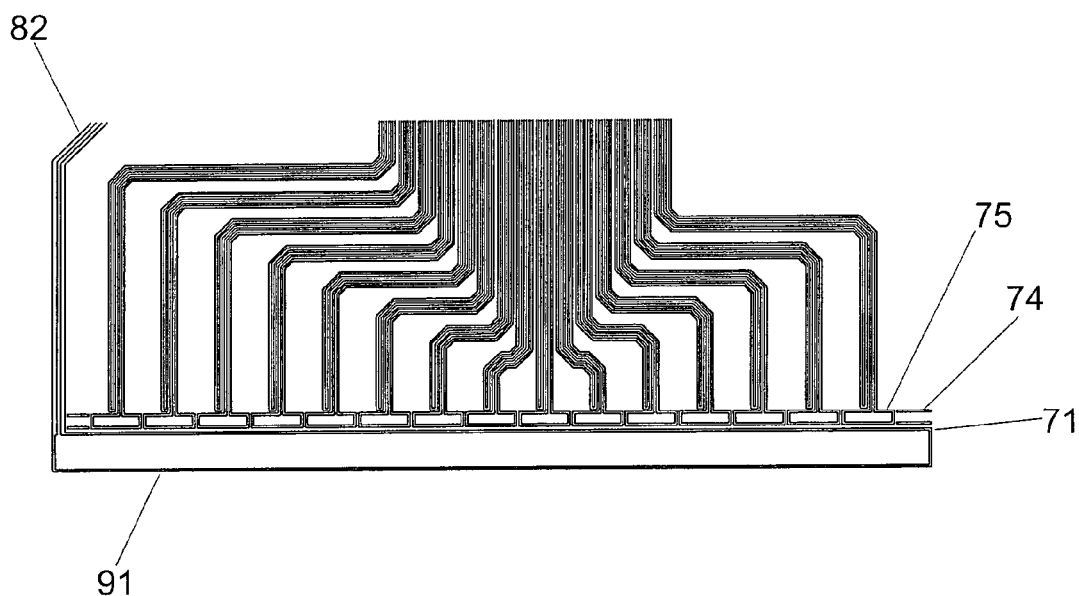
FIG. 25 is an expanded view of an eddy current array with a single rectangular loop drive winding and a linear row of sense elements on the outside of the extended portion of the loop.

In one embodiment, the number of conductors used in the primary winding can be reduced further so that a single rectangular drive is used. As shown in FIG. 25, a single loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. Advantages of the design in FIG. 25 include a narrow drive and sense structure that allows measurements close to material edges and non-crossing conductor pathways so that a single layer design can be used with all of the conductors in the sensing region in the same plane. The width of the conductor 91 farthest from the sensing elements can be made wider in order to reduce an ohmic heating from large currents being driven through the drive winding. However, this design has half the signal of the designs in FIG. 18, FIG. 20, and FIG. 22.

Figure 26:
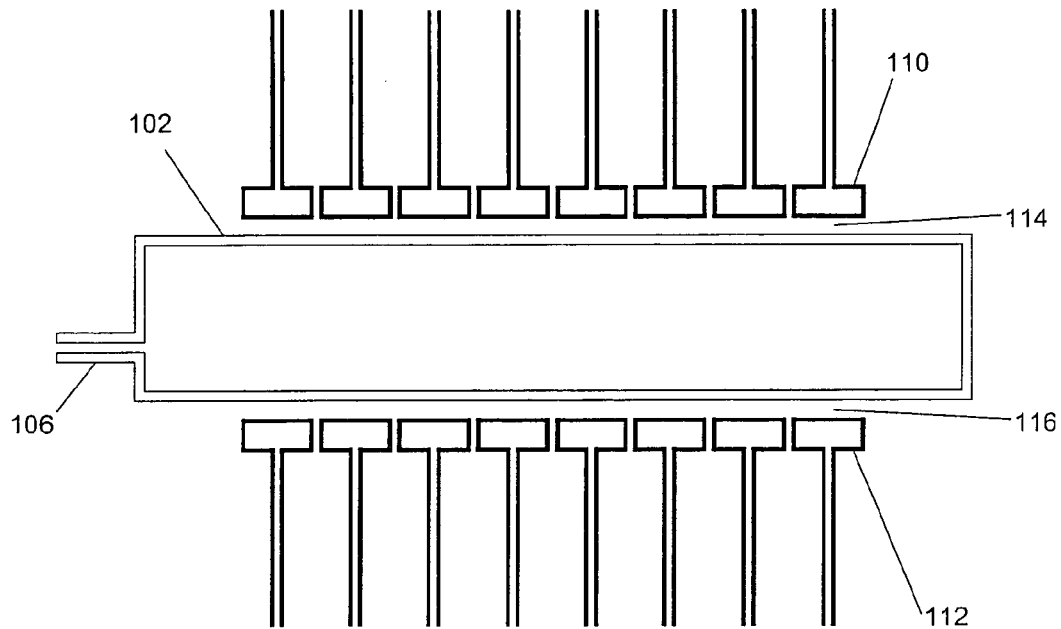
FIG. 26 is a schematic for an eddy current array with a single rectangular loop drive winding and two rows of sense elements on the outside of the extended portions.

In another embodiment, multiple rows of sensing elements are used. FIG. 26 shows a single rectangular drive winding 102 with sensing elements 110 and 112 outside of the drive winding and on either side of the extended portions of the rectangular drive. The distances 114 and 116 between the sense elements and the drive winding are selected, as described in U.S. Pat. No. 5,453,689, to provide a prescribed effective depth of penetration of the magnetic field into the MUT and a prescribed sensitivity to material properties or anomalies of interest. In an embodiment, the second row of sensing elements 112 is aligned with the first row of sensing elements 110 so that when scanning or surface mounted the array sensing elements detect the same crack or anomaly twice as it move across or propagates across the sensor. To facilitate measuring the same response from sensing elements on either side of the drive winding to an anomaly, the distances 114 and 116 should be made equal. The current source connection 106 to the drive winding should be centered so that the distance to each of the extended portions of the rectangular drive are the same. In another embodiment, shown in FIG. 27, the spacing 114 between one set of sensing elements and the drive is different than for the spacing 116 for the sensing array on the opposite side of the drive to provide two effective depths of sensitivity. This can also be accomplished with the designs in FIG. 18, FIG. 20, and FIG. 22. In another embodiment, shown in FIG. 28, the sensing elements 112 are offset from the sensing elements 110 parallel to the extended portions of the rectangular drive to improve coverage for scanning and imaging of material properties or anomalies. In a preferred embodiment, this offset distance is one-half the length of the sensing element that is parallel to the extended portions of the rectangular drive.

Figure 27:
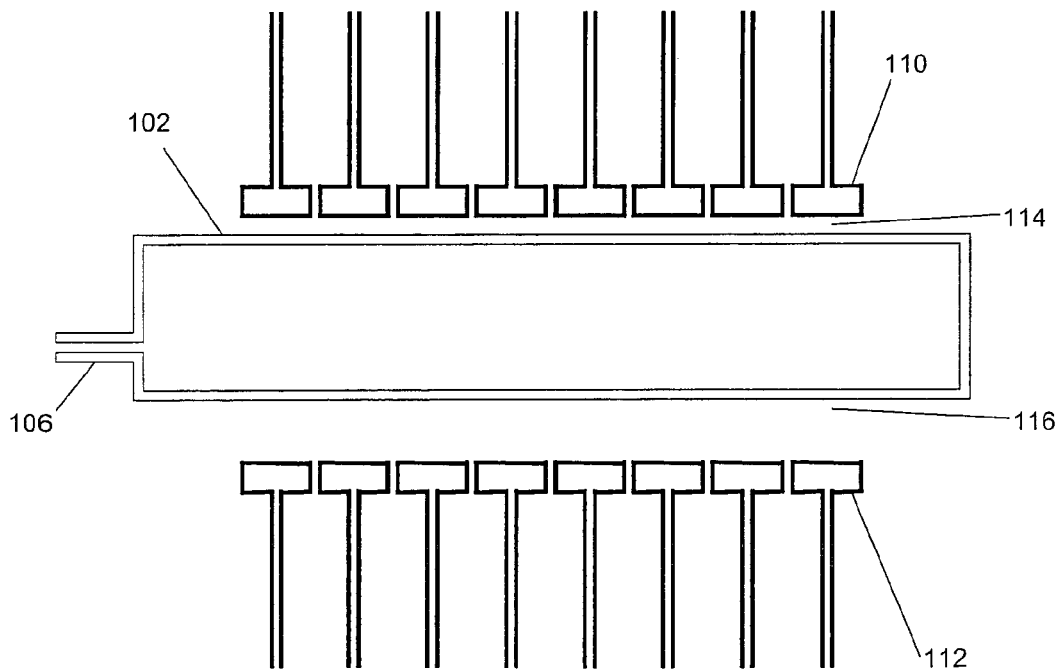
FIG. 27 is a schematic for an eddy current array with different distances between each row of sensing elements and the drive winding.
Figure 28:
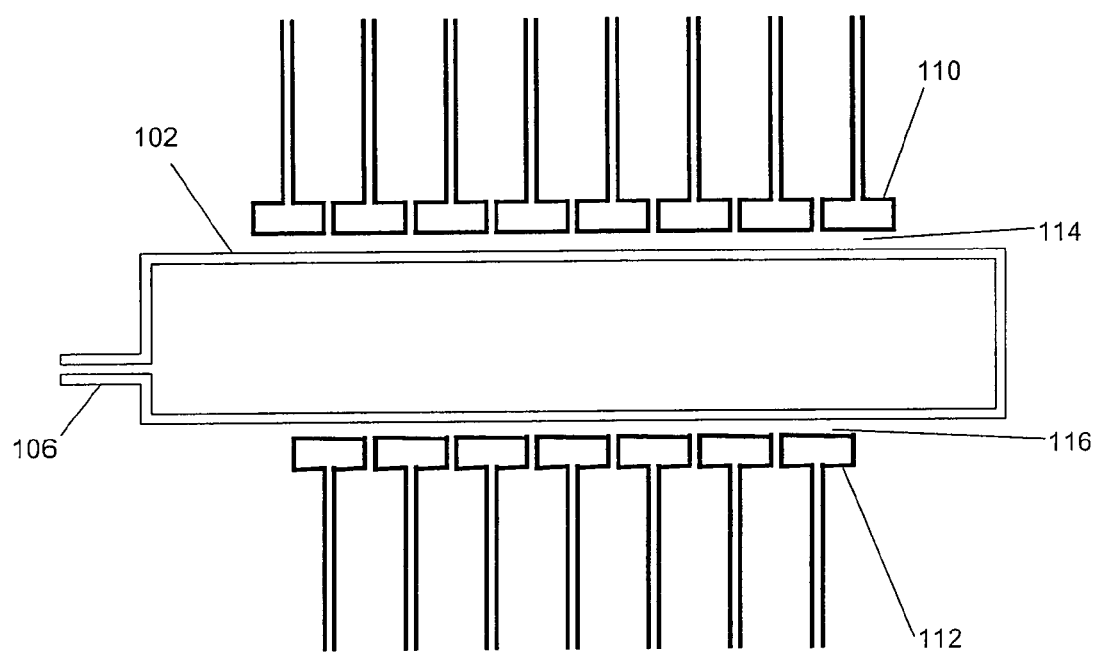
FIG. 28 is a schematic for an eddy current array with a spatial offset between each row of sensing elements, parallel to the extended portions of the drive winding.
Figure 29:
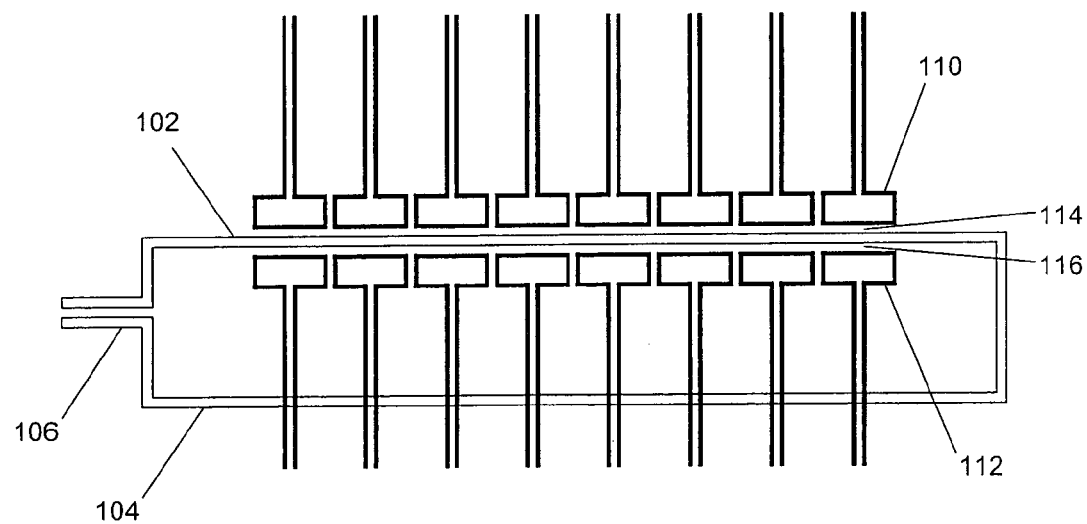
FIG. 29 is a schematic for an eddy current array having a row of sensing elements inside the drive winding loop and a row of sensing elements outside the drive winding loop.
Figure 30:
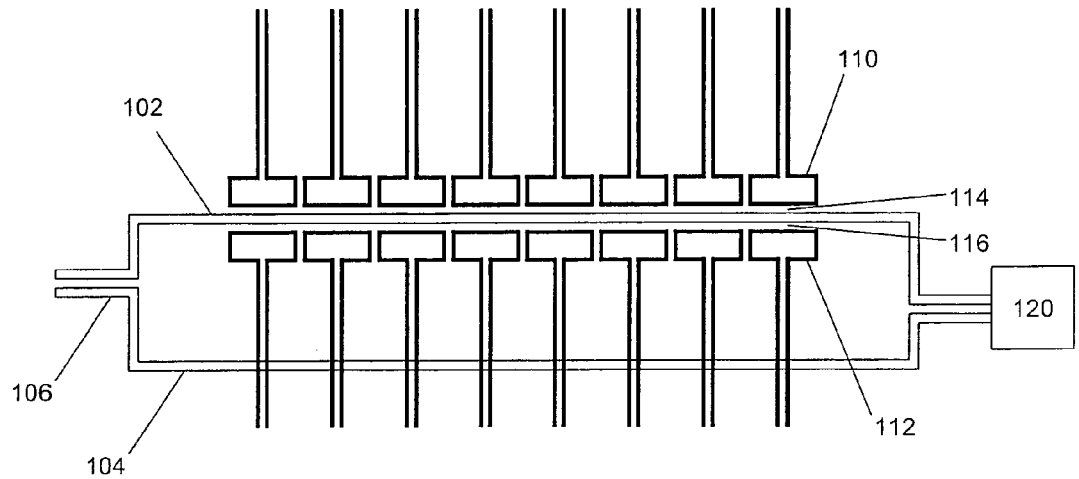
FIG. 30 is a schematic for an eddy current array with an electronic circuit at one end of the primary winding loop.

In each of the embodiments illustrated in FIG. 26, FIG. 27, and FIG. 28, the sensing elements can be placed either within the drive or on either side of the drive. These sensing elements can be placed in the same layer as the drive winding or on different layers. For sensing elements placed within the drive winding rectangle, the leads to the sensing elements must either be placed in a different layer than the drive winding conductors and separated from the drive winding conductors by a layer of insulation or the leads to the sensing elements need to pass through the back of the sensor, out of the plane formed by the drive windings. The use of flux cancellation leads, described earlier, is also preferred. An embodiment showing both rows of sensing elements close to one drive winding conductor is shown in FIG. 29. The return 104 for the drive winding is placed on a second layer. In another embodiment, shown in FIG. 30, an active or passive electronic circuit 120 is added at the opposite end of drive winding from the current source connection 106 to either amplify the current, reduce the self-inductance of the drive winding, reduce capacitive effects, or minimize thermal effects. In one embodiment, an active circuit is used to alter the resonant frequency of the drive circuit.

In a related embodiment, the single rectangular drive with one or more sensing elements is fabricated on a flexible substrate with a foam or other conformable or fluid support substrate. This substrate holds the sensor and allows it to be pressed against a curved or flat surface during scanning to measure material properties or detect defects, as described in U.S. application Ser. No. 09/946,146 filed Sep. 4, 2001, now abandoned, the entire teachings of which are incorporated herein by reference. This can be accomplished for the detection of cracks or fretting damage in engine disk slots, and the detection of cracks in bolt hole or other complex shaped MUT. The sensor can also be attached to a rigid substrate that is flat or shaped to match the curvature of an MUT. The measurements can then be performed in a non-contact scanning mode or a permanently mounted mode.

Eddy current sensor arrays are well-suited for the inspection of large areas for materials characterization (e.g., coating thickness measurements, shot peen quality assessment, and weld inspection), the detection of surface breaking and subsurface flaws (e.g., cracks and inclusions), and the detection of hidden corrosion. These sensor arrays, shown for example in FIG. 1, FIG. 11, FIG. 20, and FIG. 24, have one or more linear arrays of sensing elements oriented perpendicular to the scan direction. Then, a simple scan of the array provides a measurement image of the material properties, either in the form of the raw transimpedance magnitude and phase or in the form of effective material properties if processed with measurement grids. In contrast, the use of single element or conventional eddy current sensors requires scanning in two directions, which is more time consuming than a single direction scan but can provide higher resolution images than the linear array of discrete elements.

Figure 31:
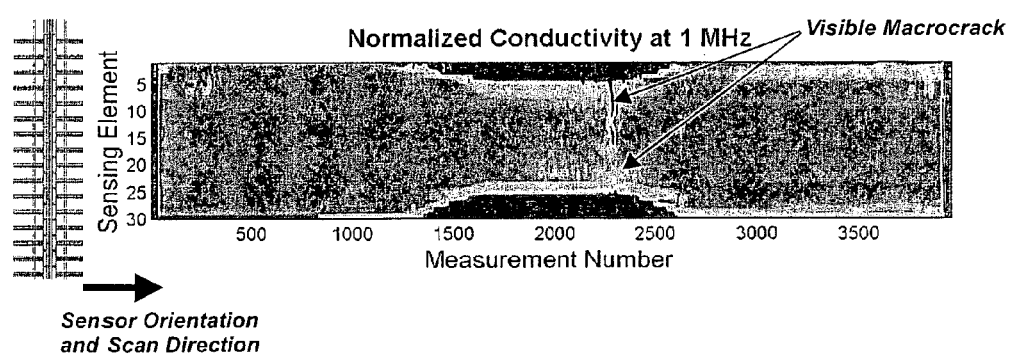
FIG. 31 shows a conductivity image for an aluminum bending fatigue specimen obtained from an MWM-Array scanned with the array drive perpendicular to the specimen axis.
Figure 32:
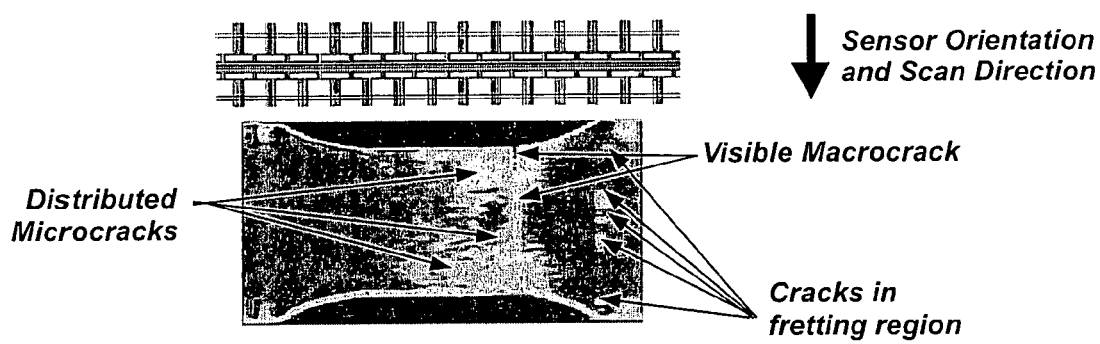
FIG. 32 shows a conductivity image for an aluminum bending fatigue specimen obtained from an MWM-Array scanned with the array drive parallel to the specimen axis.

FIG. 31 and FIG. 32 provide images showing distributed microcracks, small cracks and visible macrocracks in an aluminum bending fatigue specimen. The images are taken with the sensor in two different orientations to demonstrate the effect of the induced eddy current orientation on the sensitivity to cracks. For these specimens, the distributed small cracks are dominantly oriented perpendicular to the axis of the specimen (parallel to the bending moment axis). Consequently, FIG. 32 shows the regions of microcracking more prominently than FIG. 31.

Figure 33:
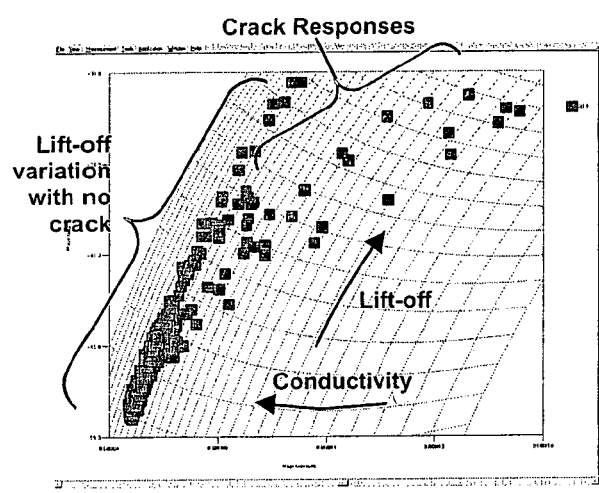
FIG. 33 shows the conductivity/lift-off measurement grid used to produce data in FIG. 32.

FIG. 33 provides the "measurement grid" used to estimate the conductivity and lift-off from the transinductance magnitude and phase data for each sensing element of the MWM-Array. For this grid, the two unknowns are the conductivity and lift-off. In this case, the model assumes the aluminum layer is an infinite half space. The data shown in FIG. 33 is for a single channel of the MWM-Array from the scan in FIG. 31.

An example subsurface defect detection application is the inspection of the C-130 flight deck chine plate for hidden corrosion. The corrosion typically occurs on the inaccessible backside of the plate while the exposed surface of the chine plate may contain, with areas of manual material removal by grinding. The plate thickness between the reinforcing ribs (stiffeners) normally ranges between 0.043 and 0.047 in.

Figure 34:
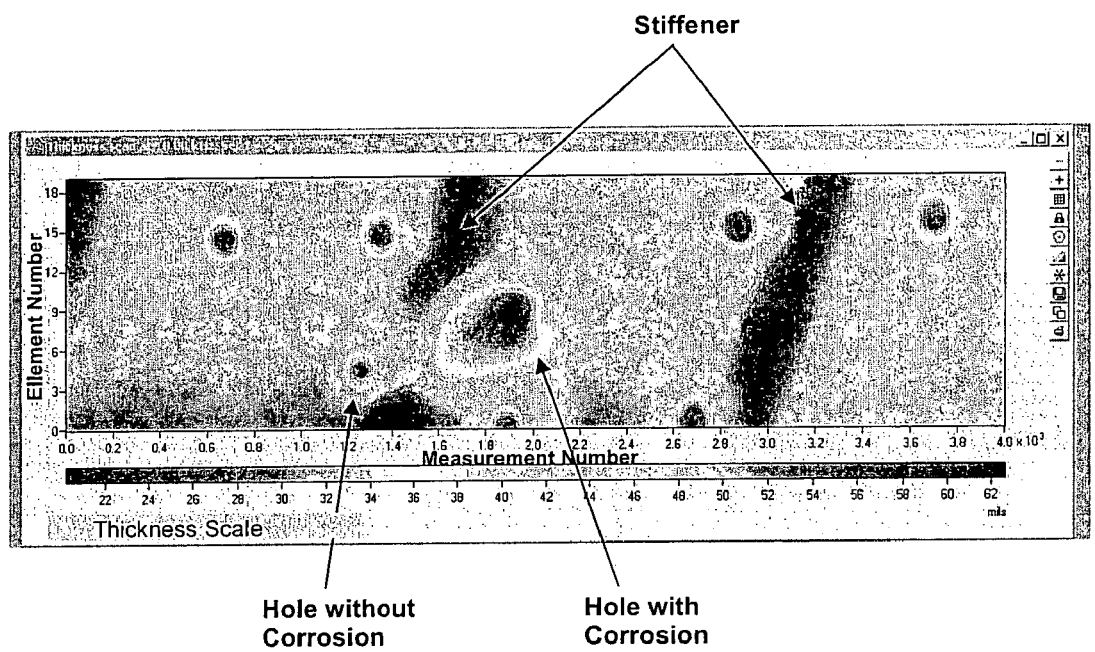
FIG. 34 shows a plate thickness image for a floor chine plate obtained with an MWM-Array and a thickness/lift-off measurement grid.
Figure 35:
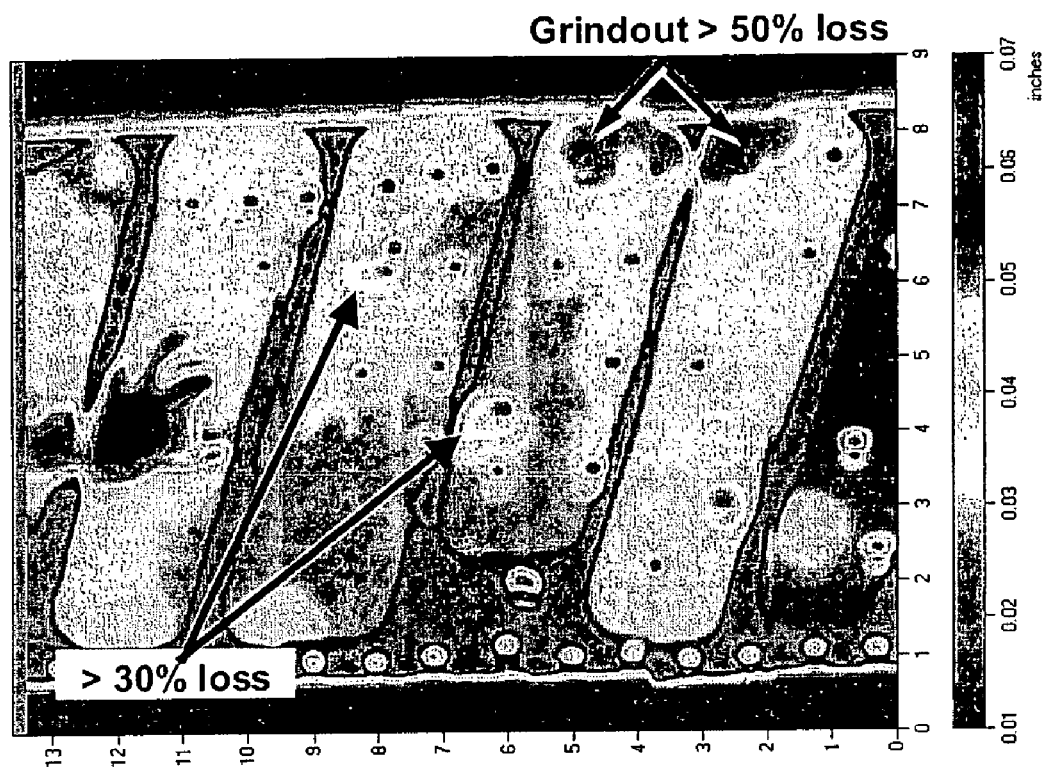
FIG. 35 shows another plate thickness image for a floor chine plate obtained with an MWM-Array and a thickness/lift-off measurement grid.
Figure 36:
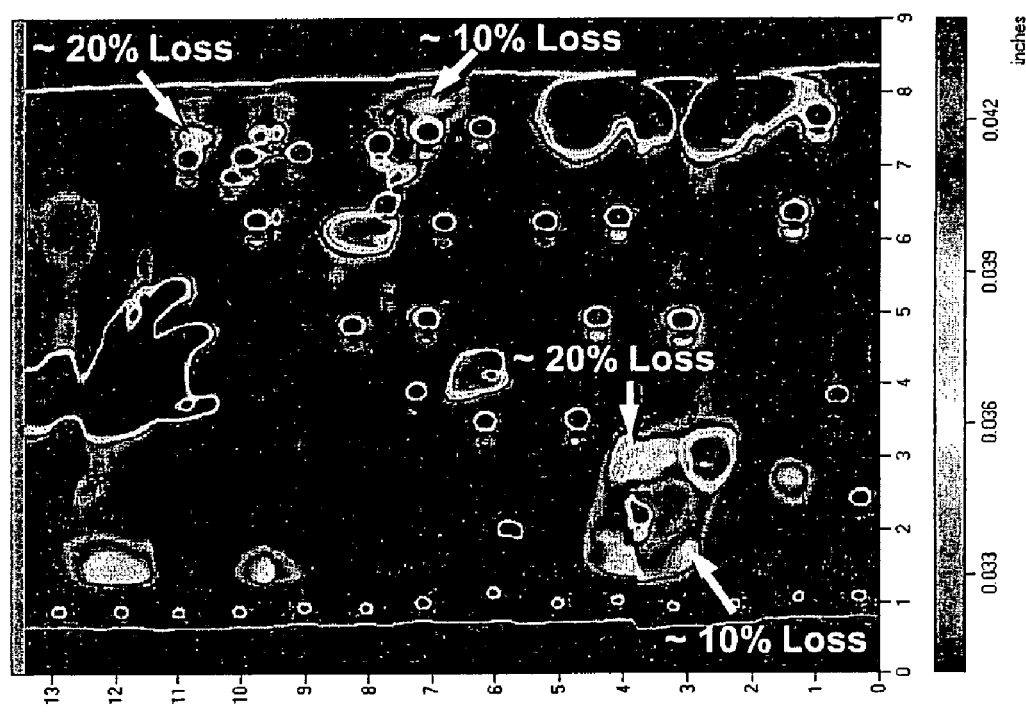
FIG. 36 shows another thickness image of the same data as in FIG. 35 with the image scale highlighting low to intermediate corrosion loss regions.

An image of the plate thickness obtained from a scan with an MWM-Array is shown in FIG. 34. Another plate thickness image is shown in FIG. 35, with FIG. 36 showing the same data with a scale highlighting low to intermediate corrosion loss regions. A measurement grid is used to convert the magnitude and phase measurements at each sensing element into estimates of plate thickness and lift-off, where lift-off is the proximity of the sensor to the outer metal surface, including contributions from roughness and paint. The result is a lift-off corrected image of the plate thickness. This permits scanning without paint removal, which is essential for the chine plate inspection application. Note that the numbers along the vertical axis in the images correspond to channel numbers. Each channel covers a 0.1-in wide area. When the MWM-Array partly overhangs the edge of the chine plate, imaging of internal geometric features and material loss close to complex features such as edges and integral stiffeners is possible. Material loss on inaccessible surface around one of the fastener holes, of 15 percent to 40 percent, is readily apparent from the image. Other work has shown that surface corrosion on the accessible surface that was manually ground out is also detectable; in some cases 50 percent to nearly 100 percent of the material has been removed in an attempt to remove the corroded areas. One new capability provided by the use of absolute sensing elements with long linear drive segments is the reduction of edge effects. By making the sensing elements small, defects and properties near and even at edges can be imaged.

Measurements performed on simulated corrosion test specimen have also demonstrated the capability of the MWM-Array to quantify and locate hidden material loss. As an example, measurements were performed on a two-layer test specimen simulating hidden corrosion in a lap joint, where the simulated material loss had a dome-shaped area machined out of one of the layers. A plate of uniform thickness then covered the domed cutout region. Measurement scans with the MWM-Array were performed on both sides of the plate so that the simulated material loss could be in either the first layer, nearest the sensor, or the second layer, farthest from the sensor. Each plate had a nominal thickness of 1 mm (0.040-in) and was fabricated from an aluminum alloy.

Figure 37:
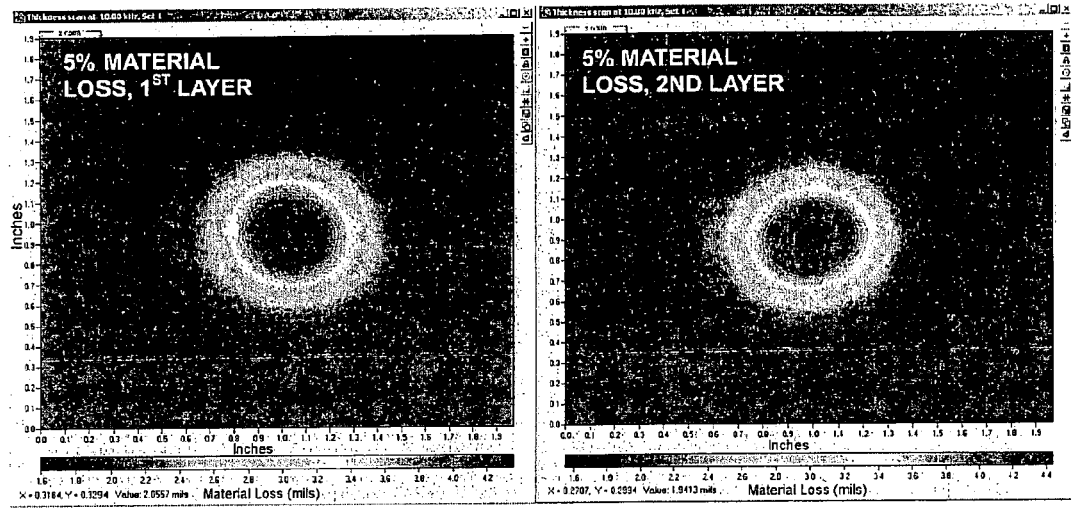
FIG. 37 shows MWM-Array generated images of the 5 percent maximum material loss, represented by a dome-shaped cavity on the inside first layer surface (left image) between two 0.04-in. thick aluminum skins; inside second layer surface (right image) between two 0.04-in. thick aluminum skins.
Figure 38:
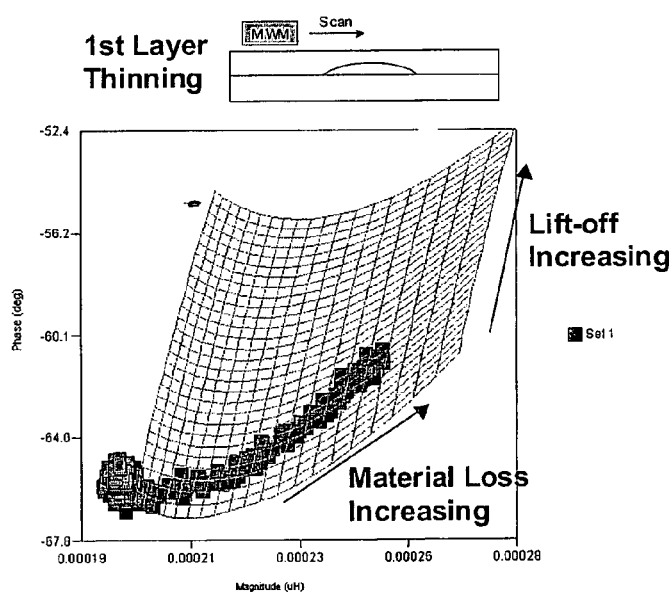
FIG. 38 shows a measurement grid and responses of a single channel of an MWM-Array to material loss between two layers as the sense element is scanned across the loss region for first layer thinning.
Figure 39:
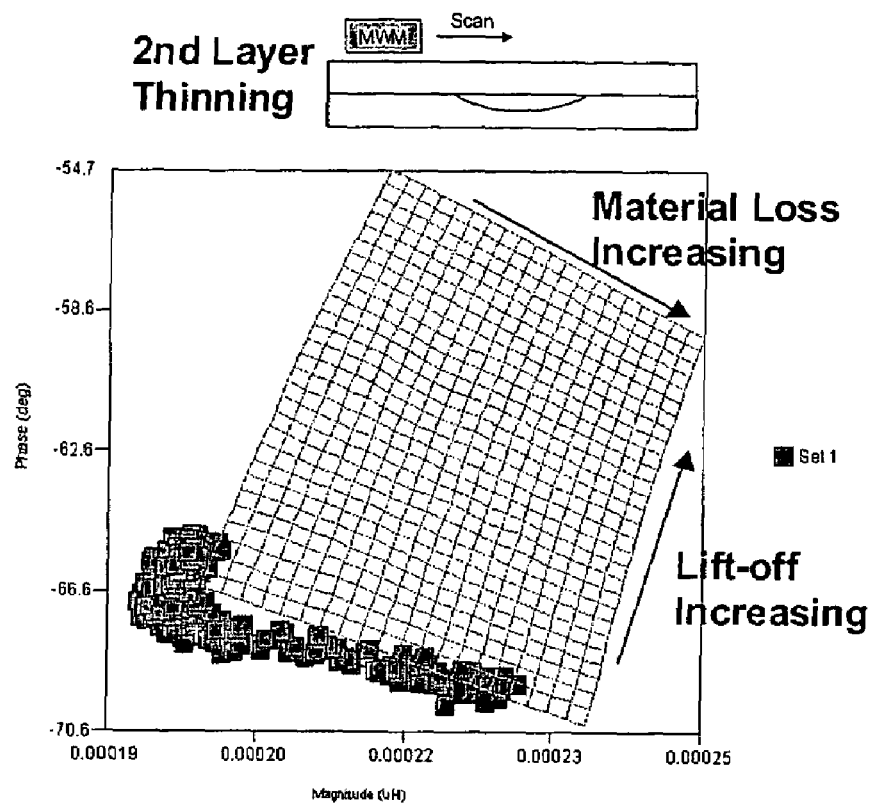
FIG. 39 shows a measurement grid and responses of a single channel of an MWM-Array to material loss between two layers as the sense element is scanned across the loss region for second layer thinning.
Figure 40:
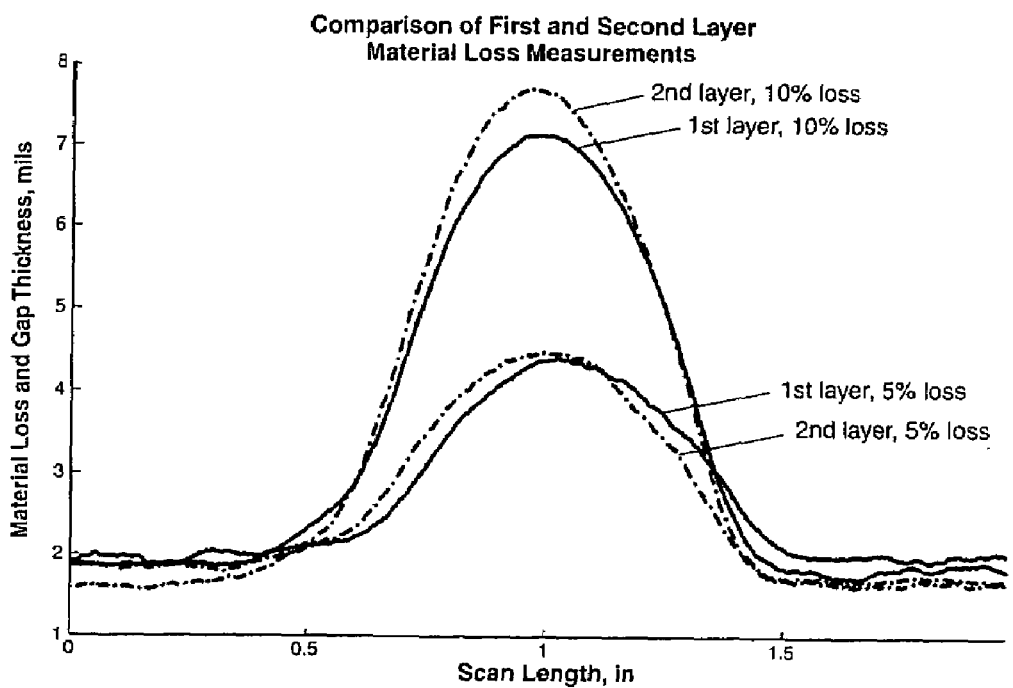
FIG. 40 shows a plot of first and second layer material loss for individual MWM sensing elements scanned across the maximum loss point for reported 5 percent and 10 percent material loss.

FIG. 37 shows images of the corrosion loss in the 5 percent loss specimens for loss in the first and second layer taken at a frequency of 10 kHz. These scan images illustrate the high resolution imaging capability of the MWM-Array and demonstrates its high sensitivity to material loss of 5 percent, with apparent sensitivity to material loss below 1 percent and relative thickness resolution potentially to a small fraction of a percent. Similar measurements were performed on higher loss samples, including 10 percent, 20 percent, and 30 percent loss. FIG. 38 and FIG. 39 show the responses of a single channel of the MWM-Array to material loss between two layers as the element is scanned across the loss region. For first or second layer material loss, the nature of the MWM-Array response varies significantly with material loss location. This variation of the response with position provides an indication of the layer in which the loss is occurring and also shows that improper assumptions regarding the location of the corrosion loss may result in errors in the material loss estimates. For corrosion detection alone, this may not be important. However, erroneous assumptions will affect sensitivity and robustness, and, for prioritization based on actual material loss percentages, it is critical to account properly for the material loss location. FIG. 40 shows a comparison of the measurements for the material loss in the first or second layers. There is good quantitative agreement between the two measurements, indicating that using an air calibration for the sensor and measurement grids based on a reasonable model for the response over the MUT can provide a robust measurement procedure. Multiple frequencies can also be used to estimate multiple unknowns, including paint thickness, first layer material loss, second layer material loss, conductivity of layers, gap thickness, and Alclad layer thickness. Also, the high resolution image produced by the MWM-Array permits (1) identification and estimation of stress concentrations (K factors) that may limit life, (2) characterization of exfoliation corrosion damage, and (3) remaining life/damage tolerance assessments.

Figure 41:
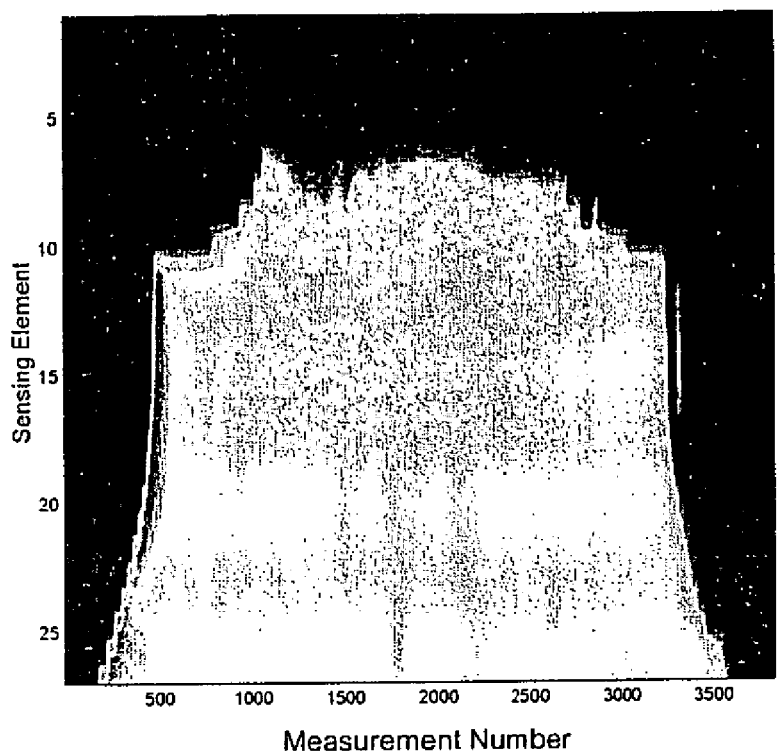
FIG. 41 shows a normalized permeability image obtained from an MWM-Array scanned over a double-notched 4340 low-alloy steel tensile specimen after failure in a tension test, with an excitation frequency of 1 MHz and the extended portions of the primary winding oriented parallel to the loading axis.
Figure 42:
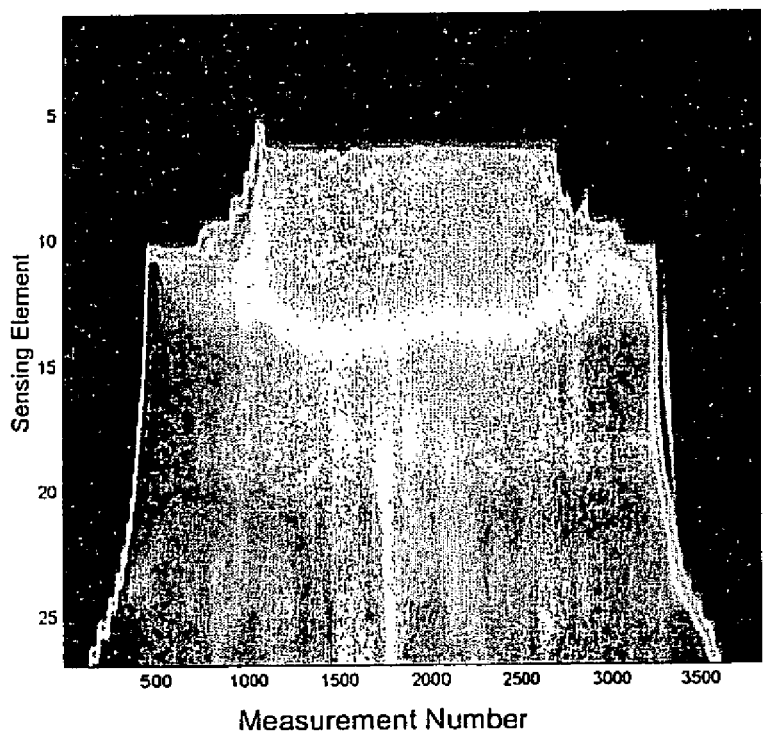
FIG. 42 shows a normalized permeability image obtained from an MWM-Array scanned over a double-notched 4340 low-alloy steel tensile specimen after failure in a tension test, with an excitation frequency of 158 kHz and the extended portions of the primary winding oriented parallel to the loading axis.
Figure 43:
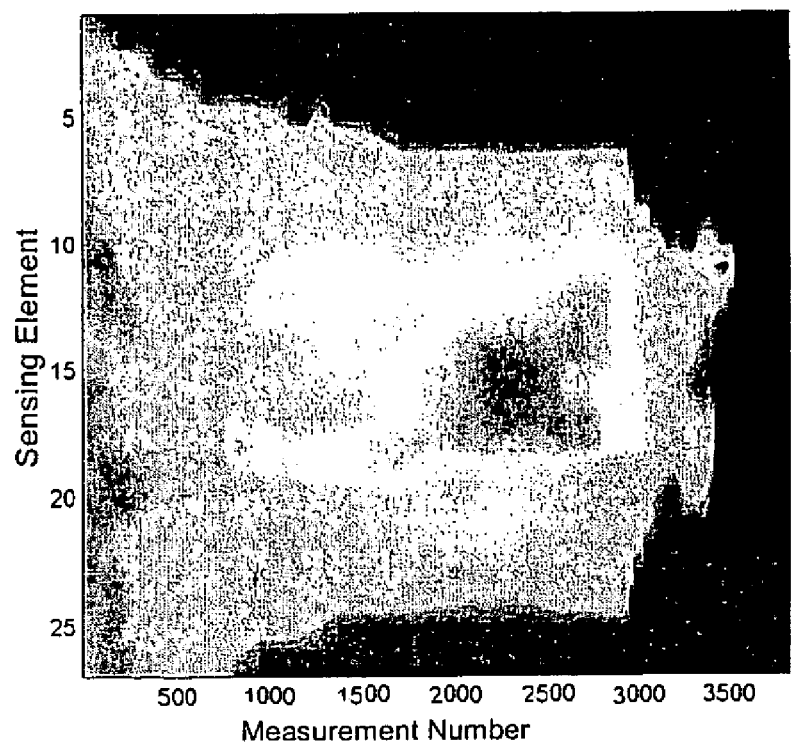
FIG. 43 shows a normalized permeability image obtained from an MWM-Array scanned over a double-notched 4340 low-alloy steel tensile specimen after failure in a tension test, with an excitation frequency of 1 MHz and the extended portions of the primary winding oriented perpendicular to the loading axis.
Figure 44:
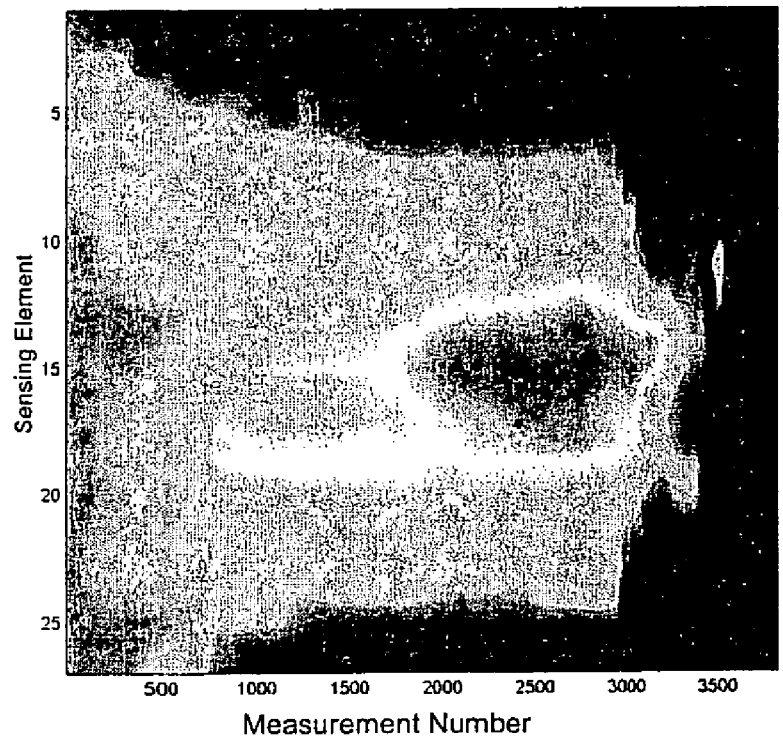
FIG. 44 shows a normalized permeability image obtained from an MWM-Array scanned over a double-notched 4340 low-alloy steel tensile specimen after failure in a tension test, with an excitation frequency of 158 kHz and the extended portions of the primary winding oriented perpendicular to the loading axis.
Figure 45:
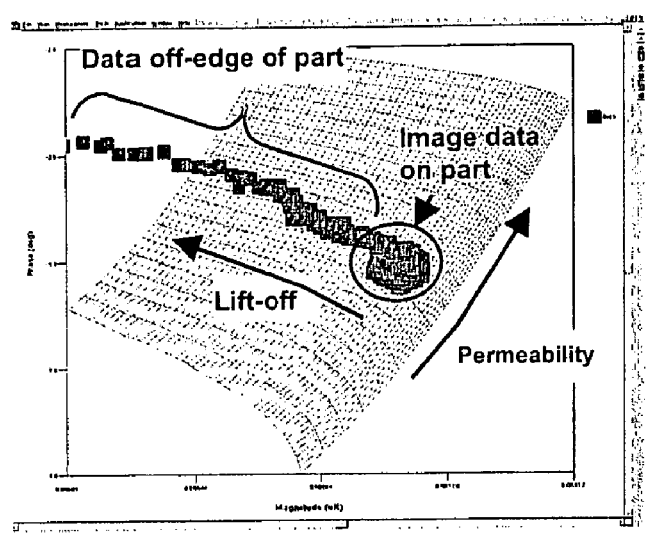
FIG. 45 shows a permeability/lift-off measurement grid and data from a single element of an MWM-Array.

MWM-Arrays also provide a capability to perform bi-directional magnetic permeability measurements in a scanning mode. FIG. 41 through FIG. 44 provide images of the magnetic permeability for a broken tensile specimen of 4340 low alloy steel. The MWM-Array was scanned across and along the gage section of a specimen broken in a tensile test and the permeability was measured at two frequencies, 158 kHz for FIG. 42 and FIG. 44 and 1 MHz for FIG. 41 and FIG. 43. In FIG. 41 and FIG. 42 the extended portions of the primary winding were oriented parallel to the loading axis. In FIG. 43 and FIG. 44 the extended portions of the primary winding were oriented perpendicular to the loading axis. This illustrates the potential to map residual stress variations produced, for example by a hard landing, in parts fabricated from carbon and low alloy steels. Notice that the permeability images at low and high frequencies reveal stress changes with distance from the surface. A high residual stress region near the fracture is indicated in the images of FIG. 43 and FIG. 44. To create these images, a permeability/lift-off measurement grid was used, as shown in FIG. 45, assuming a known conductivity and an infinite half-space (i.e., the steel layer is assumed to be infinitely thick). The relationship between permeability and stress is described in a technical paper titled "Residual and Applied Stress Estimation from Directional Magnetic Permeability Measurements with MWM Sensors" submitted to the ASME *Journal Pressure Vessels and Piping*, the entire teachings of which are incorporated herein by reference. Also, the MWM has demonstrated a capability to assess grinding process quality and detect carbide content and other metallurgical and material features of interest. Since the lift-off or distance between the sensing windings and the test material is being measured through the measurement grids, the residual stress measurement can be performed in a non-contact mode, which ensures that the sensor and probe assembly do not influence the stress distribution on the component.

The MWM construct itself was also designed to have reduced sensitivity to its own temperature so that it could operate in elevated temperature environments. The temperature affects the conductivity of the winding conductors that, in turn, affects the current distribution in the conductors. The sensitivity to winding conductivity variations with temperature is minimized by maintaining a sufficient gap between the primary and secondary windings. Then, the transverse diffusion of currents, in which the currents in the primary winding crowd out towards the winding surfacers, does not cause significant increases in inductive coupling between the primary and secondary, as described in U.S. Pat. No. 5,453,689. This also permits the use of MWM sensors and sensor arrays to measure the temperature of components. Preferably, this is done in a non-contact mode to minimize any perturbations in the thermal environment; in a contact mode, thermal heat transfer through the sensor and probe assembly could significantly affect the temperature of the component and any treatment being performed.

In another embodiment, the sensors can be designed using automated tools incorporating layout rules for the conductor pathways. This tool takes input information for the dimensions and quantity of the drive and sense elements and automatically draws the sensor layout using rules for a sensor family, such as a single element MWM, an MWM-Array, or a Rosette. In one implementation, a Matlab script processes the input information and passes it to AutoCad for the rendering the sensor design.

Another application well-suited to conformable eddy current sensor arrays is the permanent mounting of sensors in difficult-to-access locations. This provides an inspection capability that safely supports life extension for aging structures and reduces weight and maintenance/inspection costs for new structures that require both rapid and cost effective inspection capabilities. In particular, continuous monitoring of crack initiation and growth requires the permanent mounting of sensors to the component being monitored and severely limits the usefulness of calibration or reference standards, especially when placed in difficult-to-access locations on aging or new structures. Furthermore, in many difficult-to-access locations, the actual inspection is relatively short and the costly, time-consuming part is the disassembly to permit access to the location or surface preparation to remove, for example, sealant layers. In one embodiment, the capability to measure stress, through permeability, is combined with permanently mounted sensors to provide a contact or non-contact stress measurement capability.

Conventional eddy current designs are not ideal for permanent mounting. Conventional eddy-current techniques require varying the proximity of the sensor (or lift-off) to the test material or reference part by rocking the sensor back and forth or scanning across a surface to configure the equipment settings and display. For example, for crack detection the lift-off variations is generally displayed as a horizontal line, running from right to left, so that cracks or other material property variations appear on the vertical axis. Affixing or mounting the sensors against a test surface precludes this calibration routine. The probe-to-probe variability of conventional eddy-current sensors prevents calibrating with one sensor and then reconnecting the instrumentation to a second (e.g., mounted) sensor for the test material measurements. These shortcomings are overcome with spatially periodic field eddy-current sensors that provide absolute property measurements and are reproduced reliably using microfabrication techniques. Calibrations can also be performed with duplicate spatially periodic field sensors using the response in air or on reference parts prior to making the connection with the surface mounted sensor. The capability to characterize fatigue damage in structural materials, along with the continuous monitoring of crack initiation and growth, has been demonstrated, as described in U.S. application Ser. No. 09/666,879, now U.S. Pat. No. 6,657,429, and Ser. No. 09/666,524. This inspection capability is suitable for on-line fatigue tests for coupons and complex components, as well as for monitoring of difficult-to-access locations on both military and commercial aircraft.

Figure 46:
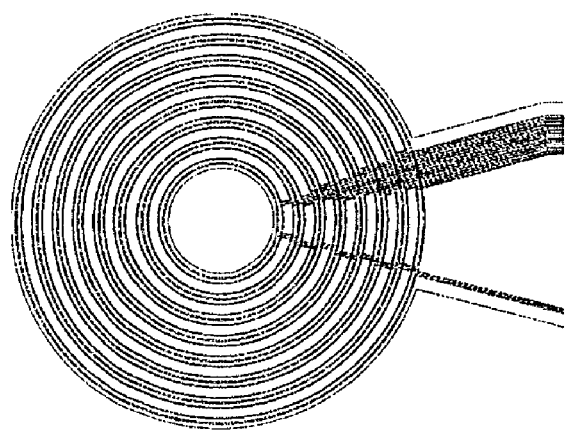
FIG. 46 shows a schematic of MWM-Rosette designed for detection of cracks at fasteners.
Figure 47:
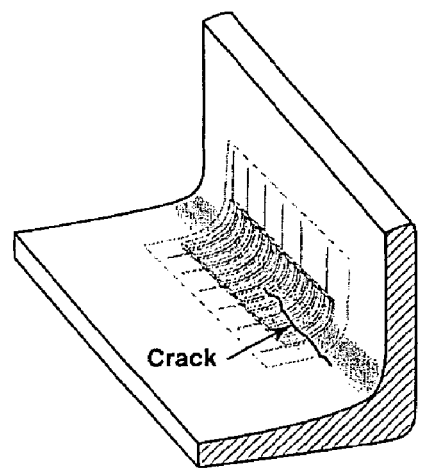
FIG. 47 shows a linear MWM-Array used to monitor crack initiation and growth along a linear feature.
Figure 48:
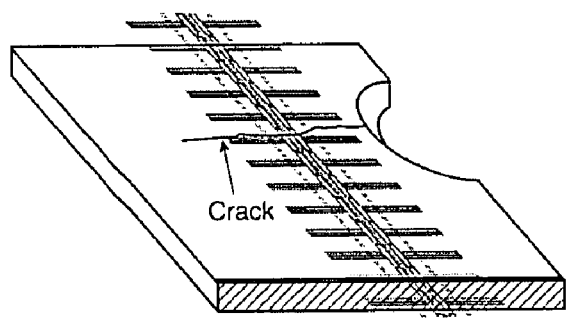
FIG. 48 shows a linear MWM-Array used to detect cracks that propagate across a specific location within a structural member.

The surface mountable MWM-Rosette shown in FIG. 46 is just one example of a sensor design suitable for surface mounting on aircraft. The design of surface mountable MWM-Arrays includes three requirements: (1) the sensing footprint must be large enough to cover the region of interest within which cracks might initiate and propagate, (2) the resolution of the sensing elements must be sufficient to monitor growth rates and estimate crack length (if more than just detection is required, subelement crack length variations can be estimated from the signal size as well), (3) at least one sensing element should be located in a region not likely to contain cracks during the inspection period. Three basic constructs for surface mounted sensors may be used: (1) the MWM-Rosette is designed for detection of cracks at fasteners as shown in FIG. 46, (2) the linear MWM-Array format shown in FIG. 47 can be used to monitor crack initiation and growth along a linear feature, e.g., a radius in an aircraft structural, and (3) the linear array format shown in FIG. 48 can be used to detect cracks that propagate across a specific location within a structure member. Each of these designs can be located on an exposed surface or sandwiched between layers (e.g., skins).

Figure 49:
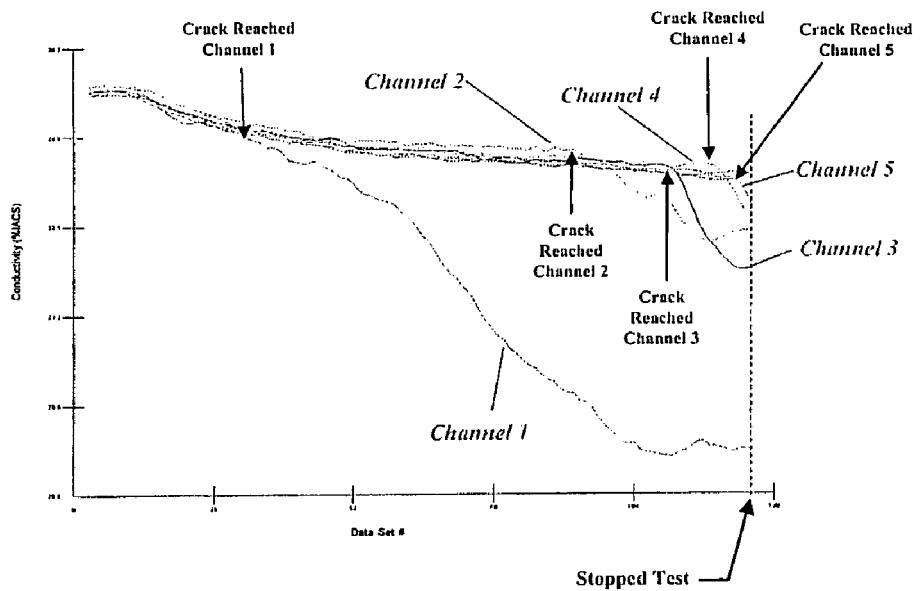
FIG. 49 shows data from a fatigue test with an MWM-Rosette mounted around a hole in an aluminum dogbone specimen, the test being stopped shortly after the crack reached channel 6.
Figure 50:
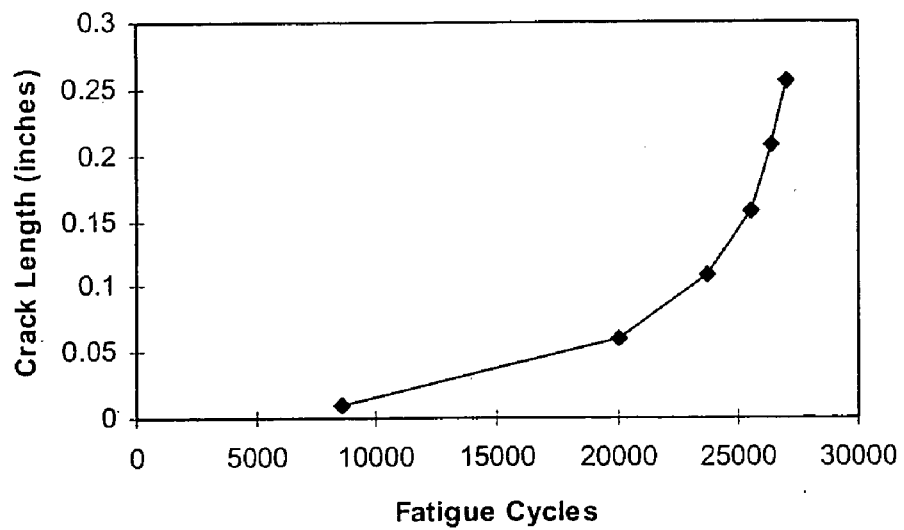
FIG. 50 shows the crack size vs. number of load cycles based on the test data shown in FIG. 49.

FIG. 49 provides data from a fatigue test with an MWM-Rosette mounted around a hole in an aluminum dogbone specimen. Each channel number corresponds to an individual annular sensing element, with channel 1 being closest to the fastener and channel 7 the furthest from the fastener. FIG. 50 shows a crack growth curve based on the data shown in FIG. 49 and known MWM-Array geometry. The conductivity drop in each channel occurs when the crack approaches the primary winding on the inner side of the sense winding.

Figure 51:
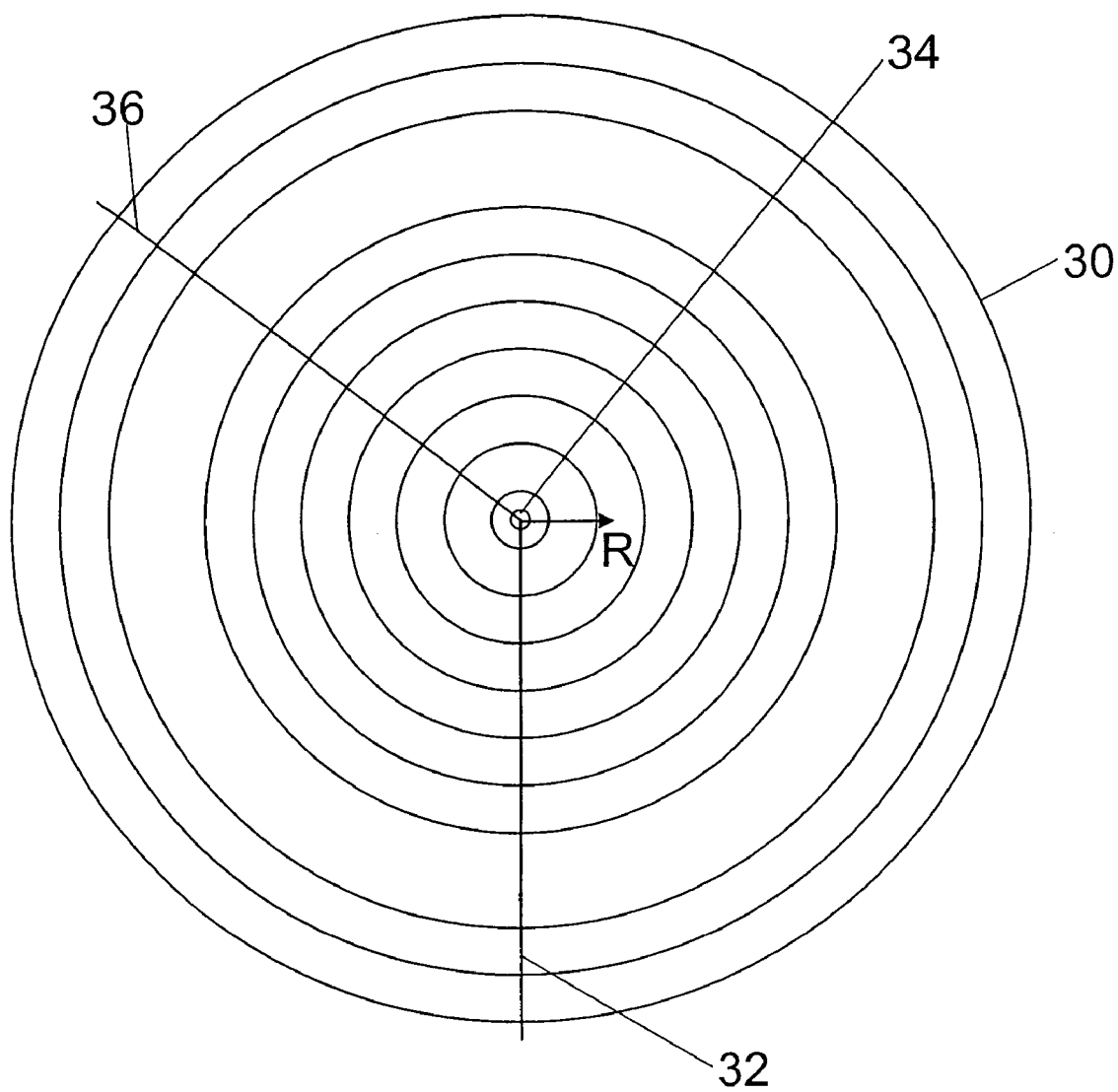
FIG. 51 shows the structure of a rotationally symmetric shaped field drive winding.

Other types of sensing elements can also be used in these arrays. The small rectangular sensing elements 72 shown, for example in FIG. 2, could be super-conducting SQUID type sensors, Hall effect probes, magnetoresistive (MR) sensors, giant magnetoresitive (GMR) sensors, or wound eddy current sensor type coils. A representative sensor that uses a GMR sensor as a sensing element and a rotationally symmetric distributed drive winding is shown in FIG. 51 and described in detail in U.S. application Ser. No. 10/045,650, filed Nov. 8, 2001, the entire teachings of which are incorporated herein by reference. For this drive winding, the number of turns in each circular winding segment 30 is varied to shape the field. Interconnections between each segment are made with tightly wound conductor pairs 32 to minimize fringing field effects. A GMR sensor 34, with feedback controlled coil, is placed at the center of the concentric circular drive windings. Connections to this hybrid sensing element are made with a tightly wound conductor pair 36. Both the number of turns and the polarity of the windings (current direction) can be varied in the drive winding segments. In this case, there are two sets of drive windings which allows more than one fundamental spatial mode. The polarity of the connection determines which of the two current drive patterns (with different fundamental spatial wavelengths) is excited. This provides two distinct field depths of penetration conditions and permits improved multiple property measurements for layered media.

Once the sensor response is obtained, an efficient method for converting the response of the GMR sensor into material or geometric properties is to use grid measurement methods. These methods map the magnitude and phase of the sensor response into the properties to be determined. The sensors are modeled, and the models are used to generate databases correlating sensor response to material properties. The measurement grids are two-dimensional databases that can be visualized as "grids" that relate two measured parameters to two unknowns, such as the conductivity and lift-off (where lift-off is defined as the proximity of the test material to the plane of the sensor windings). For coating characterization or for inhomogeneous layered constructs, three-dimensional grids (or higher order grids), called lattices (or hyper-cubes), are used. Similarly, a model for the GMR sensor with feedback loop and circular drive windings was developed and used to generate measurement grids, which were then used to interpret sensor response. Alternatively, the surface layer parameters can be determined from numerical algorithms that minimize the least-squares error between the measurements and the predicted responses from the sensor.

An advantage of the measurement grid method is that it allows for real-time measurements of the absolute electrical properties of the material. The database of the sensor responses can be generated prior to the data acquisition on the part itself, so that only table lookup operation, which is relatively fast, needs to be performed. Furthermore, grids can be generated for the individual elements in an array so that each individual element can be lift-off compensated (or compensated for variation of another unknown, such as permeability or coating thickness) to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations and instrument preparation.

Several sets of measurements have been performed with a circularly symmetric shaped field magnetometer. These measurements used the GMR eddy current sensor with drive illustrated in FIG. 51. A simple one-point air calibration method is used for all of these measurements. This means that the sensor response when over the test material was normalized by the sensor response in air, away from any conducting or magnetic materials. The measurement results are then processed with measurement grids to provide absolute property measurements, such as electrical conductivity, magnetic permeability, material thickness, and sensor proximity (lift-off). The absolute property measurement capability eliminates the need for extensive, and in some cases any, calibration sets. Even if reference calibrations are performed, possibly to improve the accuracy of the property estimation, only a single calibration material may be required. Air and reference part calibration methods have previously been described for square wave meandering winding constructs in U.S. Pat. No. 6,188,218, the contents of which are hereby incorporated in its entirety. The discrete segment Cartesian and circular geometry sensors described herein can also be calibrated in this fashion because the sensor response can be accurately modeled. In principle, air calibrations in this context can be performed with any sensor whose response can be accurately modeled.

Figure 52:
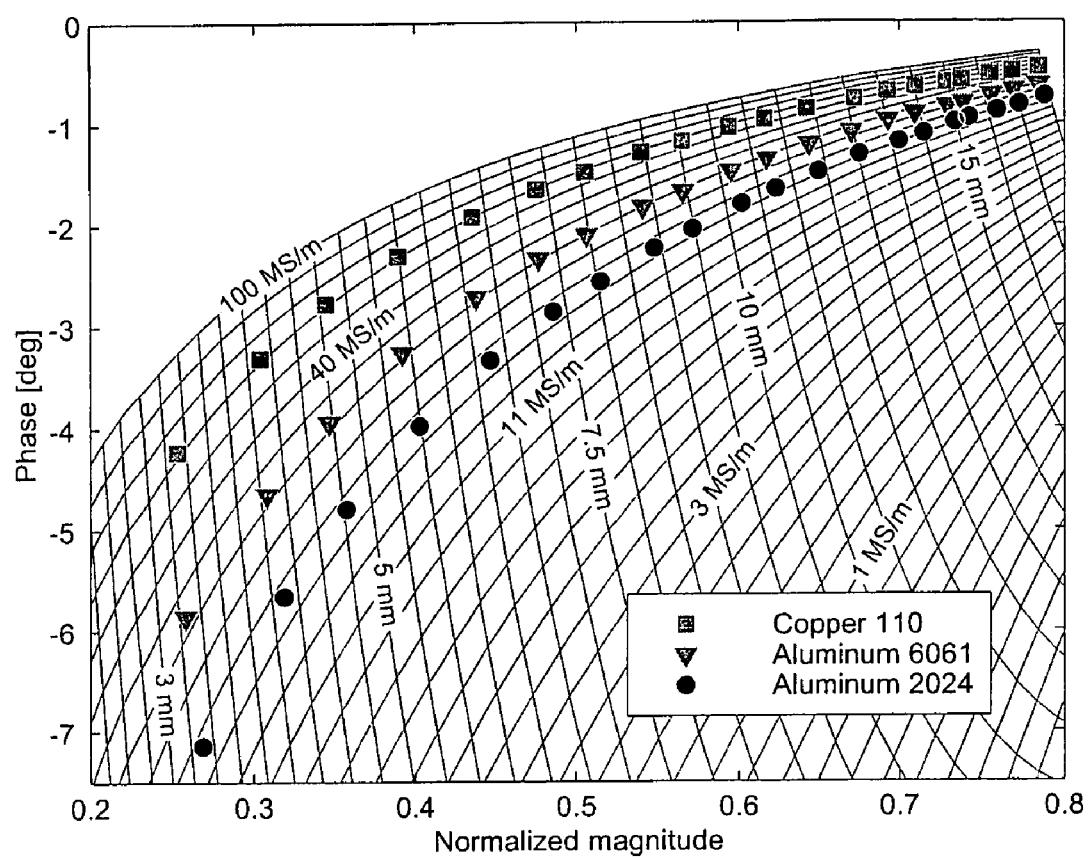
FIG. 52 shows results of conductivity/lift-off measurements with the circular magnetometer.

FIG. 52 shows the measurement grid for conductivity/lift-off measurements with three different materials, in the form of metal plates, over a range of lift-off values. Since both the conductivity and the lift-off parameters vary over a relatively large range, the parameter values for this grid are chosen on a logarithmic scale. The grid cell area is a measure of the sensitivity of the measurement in that region of the grid. The measurements are carried out at 12.6 kHz. Placing plastic shims between the sensor and the metal plates varied the lift-off. The three data sets follow lines of constant conductivity very closely. As listed in Table 1, the measured lift-off values were in excellent agreement with the nominal values. Only the first 12 sets are listed, due to the lack of sensitivity at higher lift-off values, as illustrated by the narrowing of the grid cells in FIG. 52.

The lowest value of the lift-off, 3.3 mm, corresponds to measurements with no shim, and is equal to the effective depth of the windings below the surface of the sensor. This amount has been added to the data in the last column, after having been estimated by taking the average of the difference between the magnetometer estimated values and the measured shim thicknesses. This number is quite reasonable, given that the average depth of the grooves is on the order of 3 mm, and that the winding thickness, about 2 mm, is not considered by the model. The conductivity data in Table 1 are also in good agreement with values reported in the literature. There appears to be an optimal range of the lift-off, 5–7 mm, where the estimated conductivity is most accurate. This is reasonable since sensitivity is lost at higher lift-offs, while a close proximity to the sensor windings is also not desirable since the effects of the non-zero winding thickness then become more significant. These conductivity results are also remarkable good considering that this measurement was carried out with no calibration standards and with a single air calibration point, the model for the sensor response is relatively simple, and no empirical data have been used to determine the sensor response. If it is necessary to perform a very exact conductivity measurement, then a two-point reference part calibration is recommended, with the properties of the two reference parts (or the same part at two lift-off values) bracketing the properties of the unknown part. These results confirm the validity of the model for this cylindrical coordinate sensor.

TABLE 1

Measurement results corresponding to FIG. 52.

| Data Set | Conductivity [MS/m] | | | Lift-off [mm] | | | Nominal Lift-off [mm] |
|---|---|---|---|---|---|---|---|
| | Cu 110 | Al 6061 | Al 2024 | Cu 110 | Al 6061 | Al 2024 | |
| 1 | 59.2 | 29.5 | 18.0 | 3.2 | 3.3 | 3.3 | 3.3 |
| 2 | 59.2 | 28.9 | 17.8 | 4.0 | 4.1 | 4.1 | 4.1 |
| 3 | 58.7 | 28.7 | 17.8 | 4.7 | 4.8 | 4.5 | 4.8 |
| 4 | 58.3 | 28.6 | 17.6 | 5.5 | 5.6 | 5.6 | 5.6 |
| 5 | 57.8 | 28.3 | 17.6 | 6.4 | 6.5 | 6.5 | 6.5 |
| 6 | 57.1 | 28.1 | 17.5 | 7.3 | 7.1 | 7.3 | 7.3 |
| 7 | 55.7 | 27.4 | 17.3 | 7.9 | 8.0 | 8.0 | 8.0 |
| 8 | 56.1 | 27.5 | 17.4 | 8.7 | 8.9 | 8.8 | 8.8 |
| 9 | 54.3 | 26.8 | 17.1 | 9.4 | 9.5 | 9.4 | 9.4 |
| 10 | 55.2 | 27.0 | 17.2 | 10.2 | 10.3 | 10.3 | 10.2 |
| 11 | 53.5 | 26.4 | 17.0 | 10.8 | 10.9 | 10.9 | 10.9 |
| 12 | 53.0 | 26.3 | 16.7 | 11.7 | 11.7 | 11.7 | 11.7 |

Figure 53:
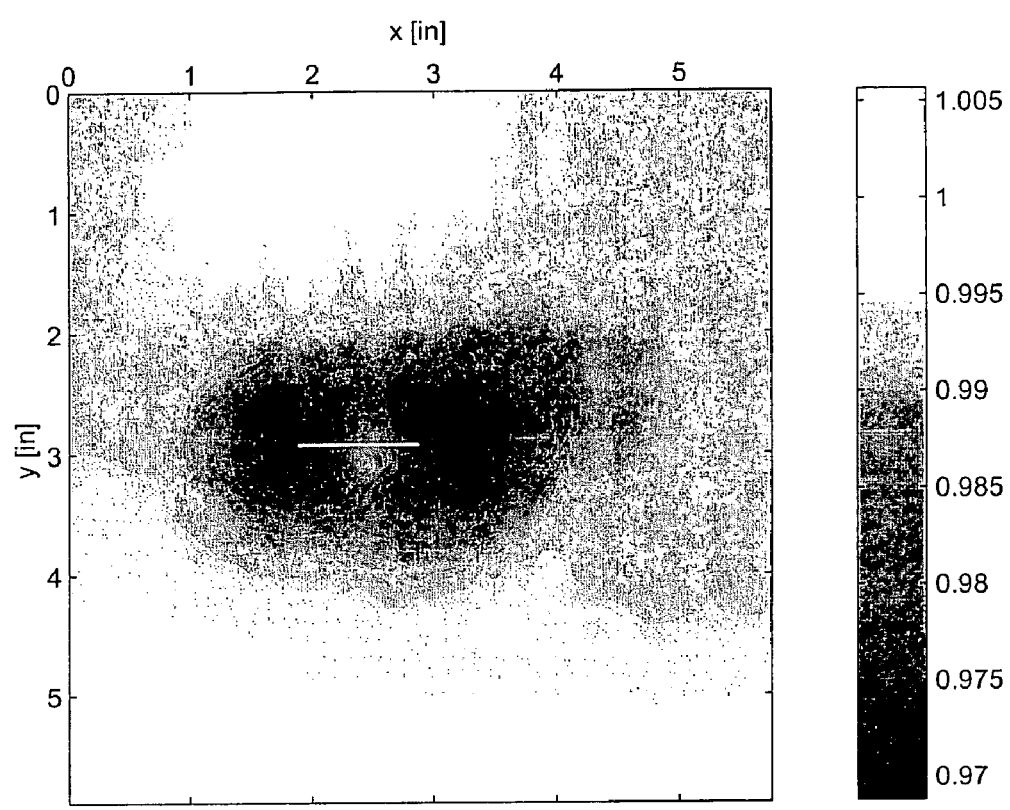
FIG. 53 shows an area scan of a stainless steel plate with the crack at the surface.

Another set of measurements illustrates the GMR magnetometer capability to detect material flaws in a thick layer of metal. These measurements were carried out by performing scans over a set of stainless steel plates. One plate had a 25 mm long, 0.4 mm wide, and 2.4 mm depth slot to simulate a crack. The crack is not modeled explicitly, but its presence is usually manifested by a local reduction in the value of the measured conductivity. In some cases, depending on its depth and position below the surface, it may appear as a local change in the lift-off. Several sets of scans were made with stainless steel plates arranged to simulate a crack at the upper surface, nearest the sensor, a crack 3.2 mm below the upper surface, and a crack 7.2 mm below the surface. The image generated by one scan, with the slot at the surface, is shown in FIG. 53. This image shows the conductivity, normalized by its value away from the crack. The crack signal is very strong, with the conductivity decreasing more than 3% near the crack position. The double hump signature of the crack is characteristic of the effect cracks have on the signal of imposed-periodicity eddy current sensors. The induced current density mirrors the current density of the drive, and as a consequence, the disruption caused by the crack is greatest when it is directly below, and perpendicular, to the primary winding nearest to the sensing element. For deeper cracks, near the crack, the measured conductivity is actually higher. This is because the phase of the induced eddy currents changes with depth. With the crack positioned 7.2 mm below the surface it interrupts eddy currents that are flowing in a direction opposite to the surface eddy currents, thereby increasing the magnetic field at the sensor. A consequence of this effect is that there is a characteristic depth, near $\pi/2$ skin depths, where a crack would cause no change in the conductivity.

Figure 54:
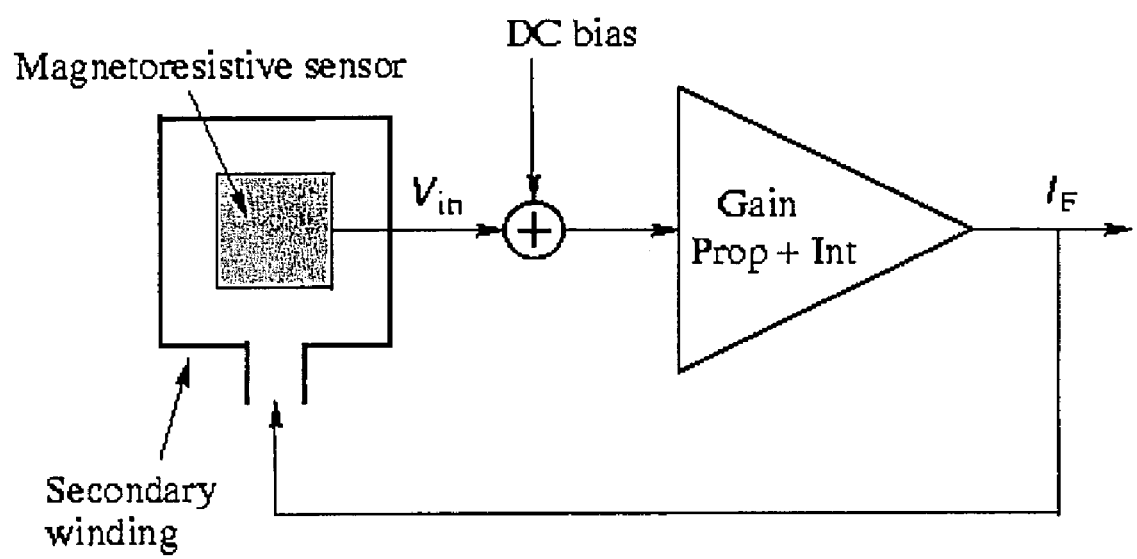
FIG. 54 shows the structure of the hybrid sensor feedback loop.

A GMR sensor can be placed in a feedback configuration with a secondary winding, as shown in FIG. 54. In this way the magnetic field at the GMR sensor remains nearly constant during operation, eliminating the effect of the nonlinear transfer characteristic, while maintaining sensitivity at low frequencies. The magnitude of the current in the secondary winding is taken as the output signal, and since the relationship between this current and the magnetic field for an air-core winding is linear, so is the transfer characteristic of the entire hybrid sensor structure. The magnetic field magnitude that this hybrid GMR sensor can measure is limited only by the magnitude of the field that the secondary winding can produce, which can be orders of magnitude higher than the saturation field of the GMR sensor. This dramatically increases the dynamic range of the GMR sensor and makes its use far more practical than in alternative implementations with permanent magnets or electromagnets that provide a constant bias.

Another benefit of the feedback configuration is temperature stability. Since the measured quantities are currents in the windings, which are directly related to the magnetic fields, temperature dependence of the GMR sensor on winding resistance, etc. has no effect on the magnetometer response. This is critical since temperature variations have limited reproducibility and limit the use of many commercially available eddy current arrays. Goldfine and Melcher (U.S. Pat. No. 5,453,689) solved the temperature sensitivity problem for inductive sensing elements by maintaining a gap between drive and sensing windings. Temperature stability is a key to the practical use of GMR sensors as well.

Another advantage of the feedback connection is for biasing the GMR sensor. Biasing the GMR sensor to the appropriate operating point is accomplished simply by adding an appropriate DC voltage offset at the input of the gain stage. This is much better than the alternative biasing methods described earlier, since correct biasing is maintained even if the position of the GMR sensor with respect to the bias source changes, which would not be true for biasing with a constant field source. This eliminates the need for complex alignment methods, since biasing at the correct level is automatic with the appropriate choice of circuit components. As a result, this feedback configuration provides the same sensitivity of a GMR sensor by itself while maintaining a linear transfer characteristic and a wider dynamic range.

Figure 55:
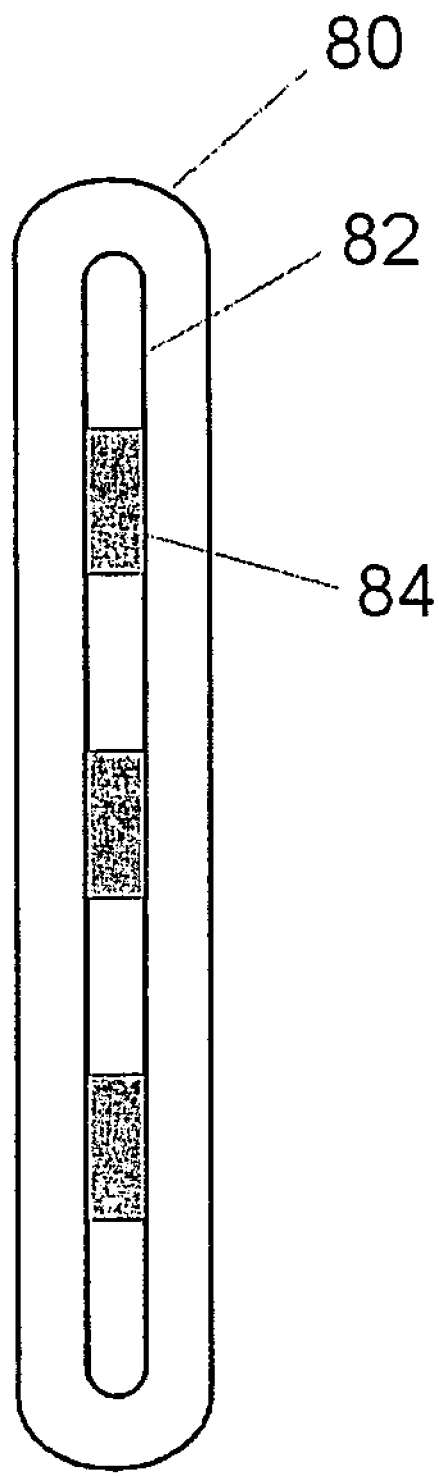
FIG. 55 shows multiple GMR sensors placed within a feedback coil and at the center of a drive winding.
Figure 56:
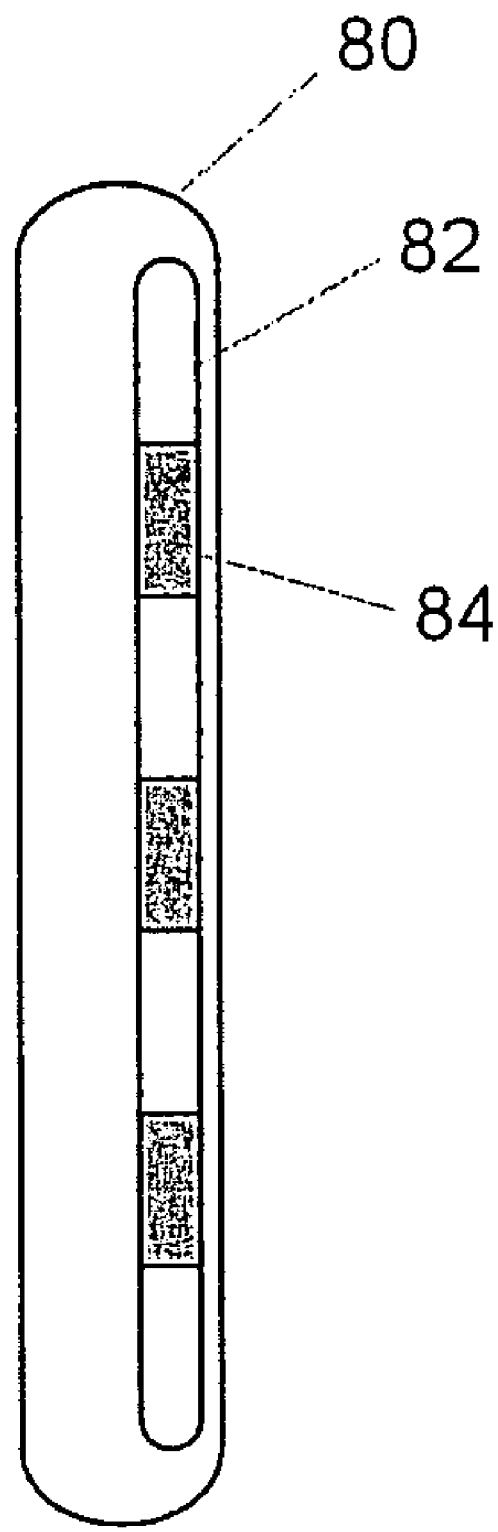
FIG. 56 shows multiple GMR sensors placed within a feedback coil and offset near an edge of a drive winding.
Figure 57:
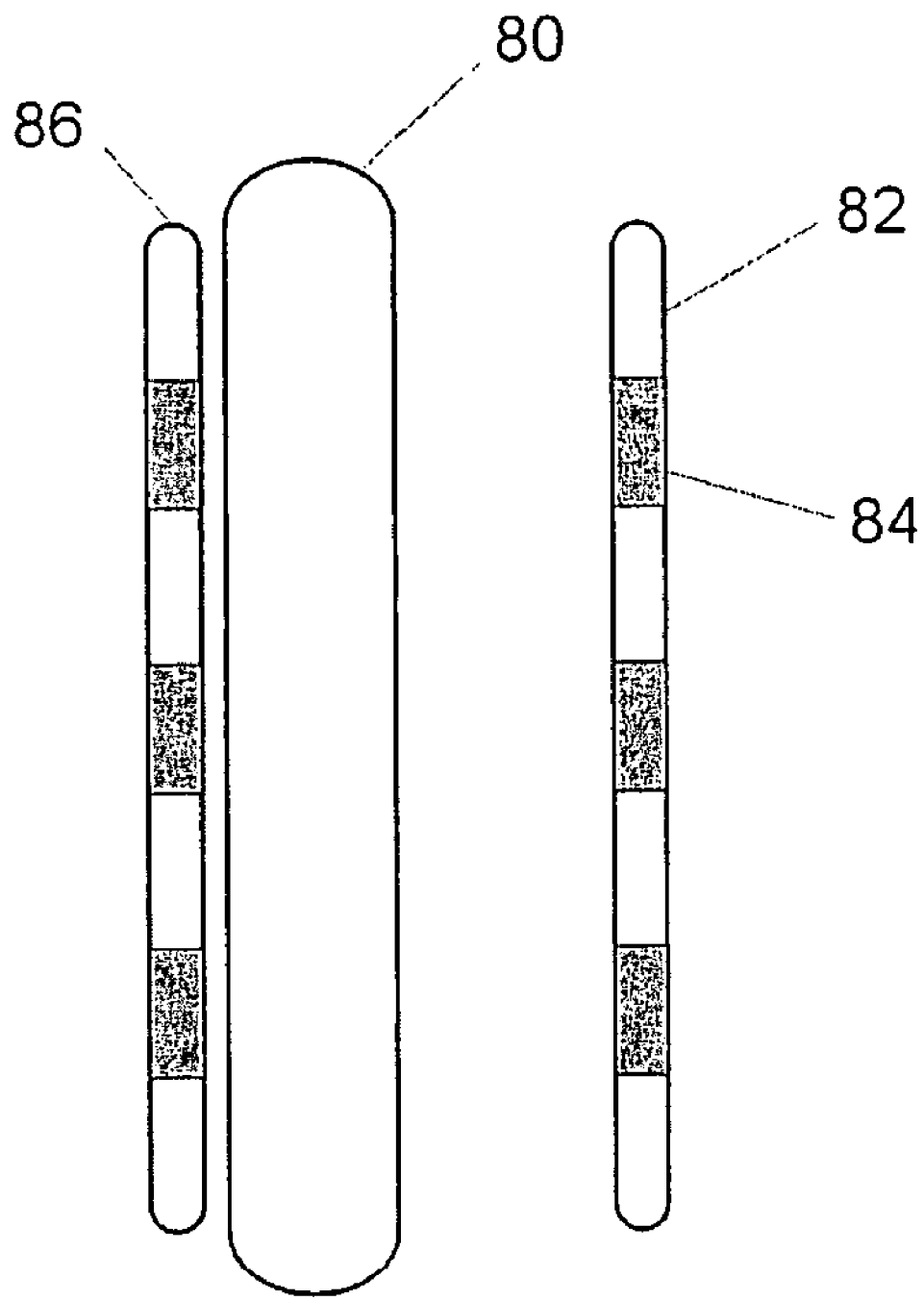
FIG. 57 shows two linear arrays of GMR sensors placed within feedback coils and external to the drive winding.

The position of the GMR elements within the feedback coil, and the position of the feedback coil within the primary winding can also be adjusted. FIG. 55 illustrates that one or more GMR sensors 84 can be surrounded by a feedback coil 82 and placed at the center of a drive winding 80. The use of multiple GMR sensors within the footprint of the drive winding promotes imaging of material properties when the array is scanned in a direction perpendicular to the row of GMR sensors. The use of a single feedback coil and multiple GMR sensor elements eliminates cross-talk between elements, which may occur if each GMR element has its own feedback coil, and also simplifies the drive circuitry for the sensor array. FIG. 56. shows a similar array with the row of GMR elements 84 and feedback coil offset so that it is closer one side of the primary winding than the other. This results in an asymmetric response when the array is scanned over a flaw since the array is more sensitive to the effects of the flaw when it passes beneath the nearer portion of the primary winding. Similarly, sensing elements can be placed outside of the drive winding, as illustrated in FIG. 57, where the row of sensor elements 84 is far from the drive winding 80 while a second row of sensors 86 is near the drive winding. An advantage of this configuration is that any connection leads to the sensing elements does not have to pass over the conductors of the drive winding, which helps to minimize parasitic responses.

The inventions described here relate to methods and apparatus for the nondestructive measurements of materials using sensors that apply electromagnetic fields to a test material and detect changes in the electromagnetic fields due to the proximity and properties of the test material. Although the discussion focused on magnetoquasistatic sensors, many of the concepts extend directly to electroquasistatic sensors as well.

While this invention has been particularly shown and described with references to preferred embodiments thereof, it will be understood by those skilled in the art that various changes in form and details may be made therein without departing from the scope of the invention encompassed by the appended claims.

The following references are incorporated herein by reference in their entirety:

Arbegast, W. J., and Hartley, P. J. (1998), "Friction Stir Weld Technology Development at Lockheed Martin Michoud Space, Systems—An Overview", $5^{th}$ International EWI Conference on Trends in Welding Research, 1–5 Jun., 1998, Pine Mountain, Ga.

Auld, B. A. and Moulder, J. C. (1999), "Review of Advances in Quantitative Eddy-Current Nondestructive Evaluation," Journal of Nondestructive Evaluation, vol. 18, No. 1.

Ditzel, P., and Lippold, J. C. (1997), "Microstructure Evolution During Friction Stir Welding of Aluminum Alloy 6061-T6", Edison Welding Institute, Summary Report SR9709.

The following references are also incorporated herein by reference in their entirety:

1. Navy Phase I Proposal, titled "Wireless Communications with Electromagnetic Sensor Networks for Nondestructive Evaluation", Topic #N01-174, dated Aug. 13, 2001.
2. Air Force Phase I Proposal, titled "Three-Dimensional Magnetic Imaging of Damage in Multiple Layer Aircraft Structures", Topic #AF02-281, dated Jan. 14, 2002.
3. Final Report submitted to FAA, titled "Crack Detection Capability Comparison of JENTEK MWM-Array and GE Eddy Current Sensors on Titanium ENSIP Plates", dated Sep. 28, 2001, Contract #DTFA03-00-C-00026, option 2 CLIN006 and 006a.
4. Technical Paper titled "Surface Mounted and Scanning Periodic Field Eddy-Current Sensors for Structural Health Monitoring", presented at the IEEE Aerospace Conference, March 2002.
5. Technical Paper titled "Corrosion Detection and Prioritization Using Scanning and Permanently Mounted MWM Eddy-Current Arrays", presented at the Tri-Service Corrosion Conference, January 2002
6. Technical Paper titled "Shaped-Field Eddy Current Sensors and Arrays", presented at the SPIE Conference, March 2002.
7. Technical paper titled "Residual and Applied Stress Estimation from Directional Magnetic Permeability Measurements with MWM Sensors," submitted to ASME Journal Pressure Vessels and Piping.
8. Technical paper titled "MWM-Array Characterization and Imaging of Combustion Turbine Components," EPRI International Conference on Advances in Life Assessment and Optimization of Fossil Power Plants, Orlando, Fla.; March 2002.
9. Presentation slides "Fatigue Test Monitoring and On-Aircraft Fatigue Monitoring Using Permanently Mounted Eddy Current Sensor Arrays," USAF ASIP Conference, Williamsburg, Va., December 2001.
10. Technical presentation slides "Condition Assessment of Engine Component Materials Using MWM-Eddy Current Sensors," ASNT Fall Conference, Columbus, Ohio; October 2001.
11. Technical presentation slides "High-Resolution Eddy Current Sensor Arrays with Inductive and Magnetoresistive Sensing Elements," ASNT Fall Conference, Columbus, Ohio; October 2001.
12. Technical presentation slides "Surface Mounted MWM-Eddy Current Sensors for Structural Health Monitoring," ASNT Fall Conference, Columbus, Ohio; October 2001.
13. Technical paper and presentation slides titled "High Throughput, Conformable Eddy-Current Sensor Arrays for Engine Disk Inspection including Detection of Cracks at Edges and in Regions with Fretting Damage," NASA/FAA/DoD Conference on Aging Aircraft, Kissimmee, Fla.; September 2001
14. Technical paper and presentation slides titled "High-Resolution Eddy Current Sensor Arrays for Detection of Hidden Damage including Corrosion and Fatigue Cracks," NASA/FAA/DoD Conference on Aging Aircraft, Kissimmee, Fla.; September 2001.
15. Technical paper titled "Flexible Eddy Current Sensors and Scanning Arrays for Inspection of Steel and Alloy Components," 7$^{th}$ EPRI Steam Turbine/Generator Workshop and Vendor Exposition, Baltimore, Md.; August 2001.
16. Technical paper titled "Conformable Eddy-Current Sensors and Arrays for Fleet-wide Gas Turbine Component Quality Assessment," ASME Turbo Expo Land, Sea & Air, New Orleans, La.; June 2001.
17. Technical presentation slides titled "Friction Stir Weld LOP Defect Detection Using New High-Resolution MWM-Arrays and MWM Eddy-Current Sensors," Aeromat 2001 Conference; June 2001.
18. Technical paper titled "Applications for Conformable Eddy Current Sensors including High Resolution and Deep Penetration Sensor Arrays in Manufacturing and Power Generation," ASME 7$^{th}$ NDE Topical Conference, San Antonio, Tex.; 2001.
19. Technical paper titled "Surface Mounted Periodic Field Current Sensors for Structural Health Monitoring," SPIE Conference: Smart Structures and Materials NDE for Health Monitoring and Diagnostics, Newport Beach, Calif.; March 2001.
20. Technical paper and presentation "Scanning and Permanently Mounted Conformable MWM Eddy Current Arrays for Fatigue/Corrosion Imaging and Fatigue Monitoring," USAF ASIP Conference, San Antonio, Tex., December 2000.
21. Technical presentation slides "Inspection of Gas Turbine Components Using Conformable MWM Eddy-Current Sensors," ASNT Fall Conference, Indianapolis, Ind.; November 2000.
22. Technical paper titled "Anisotropic Conductivity Measurements for Quality Control of C-130/P-3 Propeller Blades Using MWM Sensors with Grid Methods," Fourth DoD/FAA/NASA Conference on Aging Aircraft, St. Louis, Mo.; May 2000.
23. Technical paper titled "Surface-Mounted Eddy-Current Sensors for On-Line Monitoring of Fatigue tests and for Aircraft Health Monitoring," Second DoD/FAA/NASA Conference on Aging Aircraft, August 1998.
24. Technical paper titled "Early Stage Fatigue Detection with Application to Widespread Fatigue Damage Assessment in Military and Commercial Aircraft," First DoD/FAA/NASA Conference on Aging Aircraft, Ogden, Utah, June 1997.
25. Technical paper "Combustion Turbine Blade Coating Characterization Using a Meandering Winding Magnetometer," ASNT Fall Conference, 1994.

What is claimed is:

1. A test circuit comprising:
a primary winding of parallel conducting segments having extended portions including at least one central conductor and at least one return conductor positioned on either side of the central conductor to impose a magnetic field in a test material when driven by an electric current;
a plurality of sense elements for sensing the response of the test material to the imposed magnetic field, each sensing element positioned between the extended portions of the primary winding, the sense elements being aligned with one another to sense the response at incremental areas along a path parallel to the extended portions of the primary winding, and having separate output connections.

2. A test circuit as claimed in claim 1 wherein the distance between the central conductors and return conductors are selected to align with features of a component being tested.

3. A test circuit as claimed in claim 1 including two central conductors and two return paths symmetrically located on either side of the central conductors.

4. A test circuit as claimed in claim 3 wherein the distance between the central conductors and return conductors are selected to align with features of a component being tested.

5. A test circuit as claimed in claim 1 further comprising a second plurality of sense elements aligned with one another to sense the response at incremental areas along a path parallel to the extended portions of the primary winding, and having separate output connections.

6. A test circuit as claimed in claim 5 wherein each individual sense element in the first plurality of sense elements is aligned with a sense element in the second plurality of sense elements in a direction perpendicular to the extended portions of the primary winding.

7. A test circuit as claimed in claim 5 wherein the sense elements in the first plurality of sense elements is offset in a direction parallel to the extended portions of the primary winding from the sense elements in the second plurality of sense elements.

8. A test circuit as claimed in claim 7 wherein the offset distance is one-half of the length of a sensing element.

9. A test circuit as claimed in claim 5 wherein the distances from the first plurality of sense elements and the second plurality of sense elements to the central conductor are equal.

10. A test circuit as claimed in claim 9 wherein a differential measurement is taken between a sense element in the first plurality of sense elements and a sense element in the second plurality of sense elements.

11. A test circuit as claimed in claim 1 wherein the sensing elements and the central conductor are in the same plane.

12. A test circuit as claimed in claim 1 wherein the location of the sense elements is non-uniform in the direction parallel to the extended portions of the primary winding.

13. A test circuit as claimed in claim 1 wherein the primary winding and sense elements are fabricated onto a flexible substrate.

14. A test circuit as claimed in claim 1 further comprising a balloon filled with a fluid to maintain contact between the test circuit and a surface under test of the test material.

15. A test circuit as claimed in claim 14 wherein the balloon is attached to a shuttle and the shuttle is shaped to approximately match the shape of the material under test.

16. A test circuit as claimed in claim 15 further comprising a removable cartridge that permits rapid replacement of the sense elements and balloon components.

17. A test circuit as claimed in claim 14 wherein the surface under test is inside a bolt hole.

18. A test circuit as claimed in claim 14 wherein the surface under test is inside an engine disk slot.

19. A test circuit as claimed in claim 1 wherein the conductivity and proximity of the sensor to the surface are measured to detect cracks.

20. A test circuit as claimed in claim 1 wherein the proximity is measured at each sensing element to determine surface roughness.

21. A test circuit as claimed in claim 1 wherein each sensing element response is used for monitoring a condition of the test material.

22. A test circuit as claimed in claim 1 wherein the primary winding and sense elements are fabricated onto a rigid substrate.

23. A test circuit as claimed in claim 1 wherein the sensor is not in contact with a surface under test of the test material.

24. A test circuit as claimed in claim 1 wherein at least one of the sense elements includes a magnetoresistive sensor.

25. A test circuit as claimed in claim 1 wherein the at least one of the sense elements includes a giant magnetoresistive sensor.

26. A test circuit as claimed in claim 25 further comprising a secondary coil that surrounds the giant magnetoresistive sensing element.

27. A test circuit as claimed in claim 26 wherein the secondary coil is in a feedback configuration.

28. A test circuit as described in claim 1 wherein the sensor response to a flaw is determined in advance, this response being used to construct a filter, and the filter being applied to a sensor response to search for indications likely to be the flaw of interest and to suppress responses unlikely to be that flaw.

* * * * *